(12) United States Patent
Konishi et al.

(10) Patent No.: US 9,920,343 B2
(45) Date of Patent: Mar. 20, 2018

(54) METHOD FOR PRODUCING ANILINE DERIVATIVE BY FERMENTATION FROM CARBON SOURCE

(71) Applicant: JAPAN SCIENCE AND TECHNOLOGY AGENCY, Saitama (JP)

(72) Inventors: Kazunobu Konishi, Okayama (JP); Naoki Takaya, Ibaraki (JP); Shunsuke Masuo, Ibaraki (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 15/265,123

(22) Filed: Sep. 14, 2016

(65) Prior Publication Data
US 2017/0022528 A1    Jan. 26, 2017

Related U.S. Application Data

(63) Continuation of application No. PCT/JP2015/058295, filed on Mar. 19, 2015.

(30) Foreign Application Priority Data

Mar. 20, 2014 (JP) ................. 2014-058570

(51) Int. Cl.
     *C12P 13/22*      (2006.01)
     *C12P 13/00*      (2006.01)

(52) U.S. Cl.
CPC ........... *C12P 13/222* (2013.01); *C12P 13/001* (2013.01); *C12P 13/005* (2013.01); *C12P 13/22* (2013.01)

(58) Field of Classification Search
None
See application file for complete search history.

(56) References Cited

U.S. PATENT DOCUMENTS

| 7,109,018 | B1 | 9/2006 | Yanai et al. | |
| 7,432,102 | B2 * | 10/2008 | Yanai ...................... | C12P 17/14 435/117 |
| 2004/0214274 | A1 | 10/2004 | Yanai et al. | |
| 2008/0311631 | A1 | 12/2008 | Wubbolts et al. | |
| 2014/0323679 | A1 | 10/2014 | Kaneko et al. | |

FOREIGN PATENT DOCUMENTS

| CN | 103060352 A | 4/2013 |
| JP | 2008-501326 A | 1/2008 |
| WO | 2001/23542 A1 | 4/2001 |
| WO | 2002/077244 A1 | 3/2002 |
| WO | 2005/118829 A2 | 12/2005 |
| WO | 2013/073519 A1 | 5/2013 |

OTHER PUBLICATIONS

International Search Report dated Jun. 16, 2015 in PCT/JP2015/058295.
Mehl A. Ryan, et al., "Generation of a Bacterium with a 21 Amino Acid Genetic Code", J. Am. Chem. Soc., 2003, vol. 125, p. 935-939.
Silby W. Mark, et al., "Genomic and genetic analyses of diversity and plant interactions of Pseudomonas fluorescens", Genome Biology, 2009, vol. 10, R51.
Zhu Longbao et al., "Cloning, expression and characterization of phenylalanine ammonia-lyase from Rhodotorula glutinis", Biotechnol. Lett., 2013, vol. 35, p. 751-756.
He, et al., "The gene cluster for chloramphenicol biosynthesis in Streptomyces venezuelae ISP5230 includes novel shikimate pathway homologues and a monomodular non-ribosomal peptide synthetase gene", Microbiology (2001),147,2001, pp. 2817-2829.
Watts , et al. "Discovery of a substrate selectivity switch in tyrosine ammonia-lyase, a member of the aromatic amino acid lyase family", Chemistry & Biology, Dec. 13, 2006, pp. 1317-1326.

* cited by examiner

*Primary Examiner* — Suzanne M Noakes
(74) *Attorney, Agent, or Firm* — Perkins Coie LLP; Viola T. Kung

(57) ABSTRACT

Provided is a method for producing an aniline derivative by fermentation from a carbon source such as glucose. The method comprises the following steps: production of microorganisms capable of producing 1.8 g/L or more of 4-aminophenylalanine (4APhe) under prescribed culture conditions by introducing at least three exogenous genes into microorganisms having the ability to biosynthesize 4-aminophenylpyruvic acid from chorismic acid; and production of at least one aniline derivative selected from the group consisting of 4-aminophenylalanine (4APhe), 4-aminocinnamic acid (4ACA), 2-(4-aminophenyl)aldehyde, 4-aminophenylacetic acid, and 4-aminophenethylethanol (4APE) by bringing these microorganisms into contact with a carbon source under conditions suited to the growth and/or maintenance of these microorganisms.

8 Claims, 2 Drawing Sheets

| | |
|---|---|
| $Na_2HPO_4$ | 6.00g |
| $KH_2PO_4$ | 3.00g |
| NaCl | 0.50g |
| $NH_4Cl$ | 2.00g |
| $MgSO_4 \cdot 7H_2O$ | 0.50g |
| $CaCl_2 \cdot 2H_2O$ | 0.015g |
| Thiamine HCl | 0.05g |
| tryptone | 2.00g |
| Yeast extract | 1.00g |
| tryosine | 50.0mg |
| Tryptophan | 50.0mg |
| Trace element solution | 2.00ml |
| Distilled water | 1.00L |
| pH | 7.2 |

SEQUENCE LISTING

<160> NUMBER OF SEQ ID NOS: 28

<210> SEQ ID NO 1
<211> LENGTH: 2099
<212> TYPE: DNA
<213> ORGANISM: Artificial Sequence

```
<220> FEATURE:
<223> OTHER INFORMATION: E. coli

<400> SEQUENCE: 1
aagcttgcat gcctgcaggt cgacgttatt tggcgcgaca ttttcacggg cgtcaggggc      60
tacctggccc gcatcagctg cggcgtttgc tggccgttat tagtttgcgc tccgcatcgg     120
cagccagtgc ggcaccgcgg caaggcttag agtggcagtc agaaataatg tggccagttt     180
tgtcattttc ataggatgct cctgttatgg tcgttatgtc ggataacctc ttccaacagt     240
gcatttgcag gtgaatataa ggcattggtt taagatttca gccaggttat gaaacgcagc     300
agagaatctt gaataatta acaaacaaag gagttacagt tagaaattgt aggagagatc      360
tcgtttttcg cgacaatctg gcgttttct  tgctaattct aggattaatc cgttcatagt     420
gtaaaacccc gtttacacat tctgacggaa gatatagatt ggaagtattg cattcactaa     480
gataagtatg caacactgg aacagac atg aat tat cag aac gac gat tta cgc      534
                              Met Asn Tyr Gln Asn Asp Asp Leu Arg
                                1               5 atc aaa gaa atc aaa gag tta ctt cct cct gtc gca ttg ctg gaa aaa      582
Ile Lys Glu Ile Lys Glu Leu Leu Pro Pro Val Ala Leu Leu Glu Lys
10              15                  20                  25 ttc ccc gct act gaa aat gcc gcg aat acg gtt gcc cat gcc cga aaa      630
Phe Pro Ala Thr Glu Asn Ala Ala Asn Thr Val Ala His Ala Arg Lys
                30                  35                  40 gcg atc cat aag atc ctg aaa ggt aat gat gat cgc ctg ttg gtt gtg      678
Ala Ile His Lys Ile Leu Lys Gly Asn Asp Asp Arg Leu Leu Val Val
            45                  50                  55 att ggc cca tgc tca att cat gat cct gtc gcg gca aaa gag tat gcc      726
Ile Gly Pro Cys Ser Ile His Asp Pro Val Ala Ala Lys Glu Tyr Ala
        60                  65                  70 act cgc ttg ctg gcg ctg cgt gaa gag ctg aaa gat gag ctg gaa atc      774
Thr Arg Leu Leu Ala Leu Arg Glu Glu Leu Lys Asp Glu Leu Glu Ile
    75                  80                  85 gta atg cgc gtc tat ttt gaa aag ccg cgt acc acg gtg ggc tgg aaa      822
Val Met Arg Val Tyr Phe Glu Lys Pro Arg Thr Thr Val Gly Trp Lys
90                  95                  100                 105 ggg ctg att aac gat ccg cat atg gat aat agc ttc cag atc aac gac      870
Gly Leu Ile Asn Asp Pro His Met Asp Asn Ser Phe Gln Ile Asn Asp
                110                 115                 120 ggt ctg cgt ata gcc cgt aaa ttg ctg ctt gat att aac gac agc ggt      918
Gly Leu Arg Ile Ala Arg Lys Leu Leu Leu Asp Ile Asn Asp Ser Gly
            125                 130                 135 ctg cca gcg gca ggt gag ttt ctc gat atg atc acc cta caa tat ctc      966
Leu Pro Ala Ala Gly Glu Phe Leu Asp Met Ile Thr Leu Gln Tyr Leu
        140                 145                 150 gct gac ctg atg agc tgg ggc gca att ggc gca cgt acc acc gaa tcg     1014
Ala Asp Leu Met Ser Trp Gly Ala Ile Gly Ala Arg Thr Thr Glu Ser
    155                 160                 165 cag gtg cac cgc gaa ctg gca tca ggg ctt tct tgt ccg gtc ggc ttc     1062
Gln Val His Arg Glu Leu Ala Ser Gly Leu Ser Cys Pro Val Gly Phe
170                 175                 180                 185 aaa aat ggc acc gac ggt acg att aaa gtg gct atc gat gcc att aat     1110
Lys Asn Gly Thr Asp Gly Thr Ile Lys Val Ala Ile Asp Ala Ile Asn
                190                 195                 200 gcc gcc ggt gcg ccg cac tgc ttc ctg tcc gta acg aaa tgg ggg cat     1158
Ala Ala Gly Ala Pro His Cys Phe Leu Ser Val Thr Lys Trp Gly His
            205                 210                 215 tcg gcg att gtg aat acc agc ggt aac ggc gat tgc cat atc att ctg     1206
Ser Ala Ile Val Asn Thr Ser Gly Asn Gly Asp Cys His Ile Ile Leu
```

-continued

```
              220                 225                 230
cgc ggt ggt aaa gag cct aac tac agc gcg aag cac gtt gct gaa gtg    1254
Arg Gly Gly Lys Glu Pro Asn Tyr Ser Ala Lys His Val Ala Glu Val
    235                 240                 245 aaa gaa ggg ctg aac aaa gca ggc ctg cca gca cag gtg atg atc gat    1302
Lys Glu Gly Leu Asn Lys Ala Gly Leu Pro Ala Gln Val Met Ile Asp
250                 255                 260                 265 ttc agc cat gct aac tcg tcc aaa caa ttc aaa aag cag atg gat gtt    1350
Phe Ser His Ala Asn Ser Ser Lys Gln Phe Lys Lys Gln Met Asp Val
                270                 275                 280 tgt gct gac gtt tgc cag cag att gcc ggt ggc gaa aag gcc att att    1398
Cys Ala Asp Val Cys Gln Gln Ile Ala Gly Gly Glu Lys Ala Ile Ile
            285                 290                 295 ggc gtg atg gtg gaa agc cat ctg gtg gaa ggc aat cag agc ctc gag    1446
Gly Val Met Val Glu Ser His Leu Val Glu Gly Asn Gln Ser Leu Glu
        300                 305                 310 agc ggg gag ccg ctg gcc tac ggt aag agc atc acc gat gcc tgc atc    1494
Ser Gly Glu Pro Leu Ala Tyr Gly Lys Ser Ile Thr Asp Ala Cys Ile
    315                 320                 325 ggc tgg gaa gat acc gat gct ctg tta cgt caa ctg gcg aat gca gta    1542
Gly Trp Glu Asp Thr Asp Ala Leu Leu Arg Gln Leu Ala Asn Ala Val
330                 335                 340                 345 aaa gcg cgt cgc ggg taa ggtttaattg tcggatgcgc cgtcagagtg           1590
Lys Ala Arg Arg Gly
                350 gcgtatccga tgaatcacca caggcctgat aagtcgcgca gcgtcgcatc aggcaatgtg   1650 ctccattgtt agcaacaaaa aagccgactc acttgcagtc ggctttctca ttttaaacga   1710 atgacgttta cttcgcttta ccctggtttg caaccgccgc tgctttcgct gcgatctcgt   1770 cagcattacc cagataatag cgtttcagcg gtttgaaatt ctcgtcgaac tcatacacca   1830 gcggcacgcc agtcgggata ttaagctcaa gaatctcttc ttcgctcatg ttatcaagat   1890 atttcaccag cgcacgtaaa gagttaccgt gtgcagcgat gatcacgcgc tcaccgctct   1950 tcatacgcgg cagaatagtt tcattcctgg taagggatca cgcggtcaat ggtcagcgcc   2010 aggctttccg tcagcggcag ttctttctcg ctcagtttcg cgtaacgcgg atcgtgaccc   2070 ggatagcgct gggtaccgag ctcgaattc                                    2099
```

<210> SEQ ID NO 2
<211> LENGTH: 350
<212> TYPE: PRT
<213> ORGANISM: Artificial Sequence
<220> FEATURE:
<223> OTHER INFORMATION: E. coli

<400> SEQUENCE: 2

```
Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95
```

```
Lys Pro Arg Thr Thr Val Gly Trp Lys Gly Leu Ile Asn Asp Pro His
                100                 105                 110
Met Asp Asn Ser Phe Gln Ile Asn Asp Gly Leu Arg Ile Ala Arg Lys
            115                 120                 125
Leu Leu Leu Asp Ile Asn Asp Ser Gly Leu Pro Ala Ala Gly Glu Phe
        130                 135                 140
Leu Asp Met Ile Thr Leu Gln Tyr Leu Ala Asp Leu Met Ser Trp Gly
145                 150                 155                 160
Ala Ile Gly Ala Arg Thr Thr Glu Ser Gln Val His Arg Glu Leu Ala
                165                 170                 175
Ser Gly Leu Ser Cys Pro Val Gly Phe Lys Asn Gly Thr Asp Gly Thr
            180                 185                 190
Ile Lys Val Ala Ile Asp Ala Ile Asn Ala Ala Gly Ala Pro His Cys
        195                 200                 205
Phe Leu Ser Val Thr Lys Trp Gly His Ser Ala Ile Val Asn Thr Ser
210                 215                 220
Gly Asn Gly Asp Cys His Ile Ile Leu Arg Gly Gly Lys Glu Pro Asn
225                 230                 235                 240
Tyr Ser Ala Lys His Val Ala Glu Val Lys Glu Gly Leu Asn Lys Ala
                245                 250                 255
Gly Leu Pro Ala Gln Val Met Ile Asp Phe Ser His Ala Asn Ser Ser
            260                 265                 270
Lys Gln Phe Lys Lys Gln Met Asp Val Cys Ala Asp Val Cys Gln Gln
        275                 280                 285
Ile Ala Gly Gly Glu Lys Ala Ile Ile Gly Val Met Val Glu Ser His
        290                 295                 300
Leu Val Glu Gly Asn Gln Ser Leu Glu Ser Gly Glu Pro Leu Ala Tyr
305                 310                 315                 320
Gly Lys Ser Ile Thr Asp Ala Cys Ile Gly Trp Glu Asp Thr Asp Ala
                325                 330                 335
Leu Leu Arg Gln Leu Ala Asn Ala Val Lys Ala Arg Arg Gly
                340                 345                 350

<210> SEQ ID NO 3
<211> LENGTH: 110
<212> TYPE: DNA
<213> ORGANISM: Artificial Sequence
<220> FEATURE:
<223> OTHER INFORMATION: Synthesized

<400> SEQUENCE: 3
gatgattcac atcatccggc acctttcat caggttggat caacaggcac gaagttccta     60
tactttctag agagaatagg aacttctcag aagaactcgt caagaaggcg              110

<210> SEQ ID NO 4
<211> LENGTH: 109
<212> TYPE: DNA
<213> ORGANISM: Artificial Sequence
<220> FEATURE:
<223> OTHER INFORMATION: Synthesized

<400> SEQUENCE: 4
gtgaaaacag tacgggtact gtactaaagt cacttaagga aacaaacatg gaagttccta     60
ttctctagaa agtataggaa cttctggaca gcaagcgaac cggaattgc                109

<210> SEQ ID NO 5
```

<211> LENGTH: 882
<212> TYPE: DNA
<213> ORGANISM: Artificial Sequence
<220> FEATURE:
<223> OTHER INFORMATION: Pseudomonas fluorescence

<400> SEQUENCE: 5

```
cat atg aac acg aac acg gtg gtg gtg ctg ggc ggc gct ggt ctg att      48
    Met Asn Thr Asn Thr Val Val Val Leu Gly Gly Ala Gly Leu Ile
    1               5                   10                  15 ggc tcc atg atc tct cgc atc ctg aaa cag tac ggc tac ttt gtg cgt      96
Gly Ser Met Ile Ser Arg Ile Leu Lys Gln Tyr Gly Tyr Phe Val Arg
                20                  25                  30 gtg gtt gat cgt cgc ccg gcc gaa ttc gaa tgc gaa tat cat gaa atg     144
Val Val Asp Arg Arg Pro Ala Glu Phe Glu Cys Glu Tyr His Glu Met
            35                  40                  45 gat gtc acc aaa ccg ttt aac gac acc ggt gcc gtg ttc cgt aat gct     192
Asp Val Thr Lys Pro Phe Asn Asp Thr Gly Ala Val Phe Arg Asn Ala
        50                  55                  60 acc gcc gtc gtg ttt gca ctg ccg gaa agc gtg gcc gtt tct gca att     240
Thr Ala Val Val Phe Ala Leu Pro Glu Ser Val Ala Val Ser Ala Ile
    65                  70                  75 ccg tgg gtt acc acg ttc ctg agc tct gaa gtt gtc ctg atc ccg acg     288
Pro Trp Val Thr Thr Phe Leu Ser Ser Glu Val Val Leu Ile Pro Thr
80                  85                  90                  95 tgt tca gtg cag ggt ccg ttt tac aaa gct ctg aaa gcc gcg gca ccg     336
Cys Ser Val Gln Gly Pro Phe Tyr Lys Ala Leu Lys Ala Ala Ala Pro
                100                 105                 110 cgt caa ccg ttt gtc ggt gtg aac ccg atg ttc agt ccg aaa ctg tcc     384
Arg Gln Pro Phe Val Gly Val Asn Pro Met Phe Ser Pro Lys Leu Ser
            115                 120                 125 gtt cag ggt cgt tca gtt gcg gtc tgc gtg gaa gat acc cag gct gcg     432
Val Gln Gly Arg Ser Val Ala Val Cys Val Glu Asp Thr Gln Ala Ala
        130                 135                 140 cag acc ttt att gaa cgc cat ctg atg gaa gct ggc atg aaa atc cgt     480
Gln Thr Phe Ile Glu Arg His Leu Met Glu Ala Gly Met Lys Ile Arg
    145                 150                 155 cgc atg acc ccg tcg gcg cat gac gaa ctg atg gct ctg tgc cag gcg     528
Arg Met Thr Pro Ser Ala His Asp Glu Leu Met Ala Leu Cys Gln Ala
160                 165                 170                 175 ctg ccg cat gca gca att ctg ggc ttt ggt atg gcc ctg gca aaa agt     576
Leu Pro His Ala Ala Ile Leu Gly Phe Gly Met Ala Leu Ala Lys Ser
                180                 185                 190 tcc gtg gat atg gac atc gtt gcc gaa gtc atg ccg ccg cca atg cgt     624
Ser Val Asp Met Asp Ile Val Ala Glu Val Met Pro Pro Pro Met Arg
            195                 200                 205 acc atg atg gca ctg ctg agc cgc att ctg gtg aac ccg ccg gaa gtt     672
Thr Met Met Ala Leu Leu Ser Arg Ile Leu Val Asn Pro Pro Glu Val
        210                 215                 220 tat tgg gat atc cag ctg gaa aat gac cag gct acg gcg caa cgt gat     720
Tyr Trp Asp Ile Gln Leu Glu Asn Asp Gln Ala Thr Ala Gln Arg Asp
    225                 230                 235 gcc ctg gtt cac ggt ctg gaa cgc ctg cag gaa aat att gtc gaa caa     768
Ala Leu Val His Gly Leu Glu Arg Leu Gln Glu Asn Ile Val Glu Gln
240                 245                 250                 255 gat tac gaa cgc ttt aaa tct gac ctg caa tca gtg tcg acc gca ctg     816
Asp Tyr Glu Arg Phe Lys Ser Asp Leu Gln Ser Val Ser Thr Ala Leu
                260                 265                 270 ggt aaa cgc ctg aac gct ggt gcc gtg gat tgt caa cac ctg ttt tcc     864
Gly Lys Arg Leu Asn Ala Gly Ala Val Asp Cys Gln His Leu Phe Ser
            275                 280                 285
```

```
ctg ctg aac taa ctcgag                                              882
Leu Leu Asn
        290
```

<210> SEQ ID NO 6
<211> LENGTH: 290
<212> TYPE: PRT
<213> ORGANISM: Artificial Sequence
<220> FEATURE:
<223> OTHER INFORMATION: Pseudomonas fluorescence

<400> SEQUENCE: 6

| Met | Asn | Thr | Asn | Thr | Val | Val | Leu | Gly | Gly | Ala | Gly | Leu | Ile | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Met Ile Ser Arg Ile Leu Lys Gln Tyr Gly Tyr Phe Val Arg Val
             20                  25                  30

Val Asp Arg Arg Pro Ala Glu Phe Glu Cys Glu Tyr His Glu Met Asp
         35                  40                  45

Val Thr Lys Pro Phe Asn Asp Thr Gly Ala Val Phe Arg Asn Ala Thr
     50                  55                  60

Ala Val Val Phe Ala Leu Pro Glu Ser Val Ala Val Ser Ala Ile Pro
65                  70                  75                  80

Trp Val Thr Thr Phe Leu Ser Ser Glu Val Val Leu Ile Pro Thr Cys
                 85                  90                  95

Ser Val Gln Gly Pro Phe Tyr Lys Ala Leu Lys Ala Ala Pro Arg
            100                 105                 110

Gln Pro Phe Val Gly Val Asn Pro Met Phe Ser Pro Lys Leu Ser Val
        115                 120                 125

Gln Gly Arg Ser Val Ala Val Cys Val Glu Asp Thr Gln Ala Ala Gln
    130                 135                 140

Thr Phe Ile Glu Arg His Leu Met Glu Ala Gly Met Lys Ile Arg Arg
145                 150                 155                 160

Met Thr Pro Ser Ala His Asp Glu Leu Met Ala Leu Cys Gln Ala Leu
                165                 170                 175

Pro His Ala Ala Ile Leu Gly Phe Gly Met Ala Leu Ala Lys Ser Ser
            180                 185                 190

Val Asp Met Asp Ile Val Ala Glu Val Met Pro Pro Met Arg Thr
        195                 200                 205

Met Met Ala Leu Leu Ser Arg Ile Leu Val Asn Pro Pro Glu Val Tyr
    210                 215                 220

Trp Asp Ile Gln Leu Glu Asn Asp Gln Ala Thr Ala Gln Arg Asp Ala
225                 230                 235                 240

Leu Val His Gly Leu Glu Arg Leu Gln Glu Asn Ile Val Glu Gln Asp
                245                 250                 255

Tyr Glu Arg Phe Lys Ser Asp Leu Gln Ser Val Ser Thr Ala Leu Gly
            260                 265                 270

Lys Arg Leu Asn Ala Gly Ala Val Asp Cys Gln His Leu Phe Ser Leu
        275                 280                 285

Leu Asn
    290

<210> SEQ ID NO 7
<211> LENGTH: 2079
<212> TYPE: DNA
<213> ORGANISM: Artificial Sequence
<220> FEATURE:
<223> OTHER INFORMATION: Pseudomonas fluorescence

<400> SEQUENCE: 7

```
cat atg aaa att ctg ctg att gac aac ttt gat tcc ttt acc caa aac      48
    Met Lys Ile Leu Leu Ile Asp Asn Phe Asp Ser Phe Thr Gln Asn
    1               5                   10                  15 atc gct cag tat ctg tac gaa gtg acg ggc atc tgc gcc gac att gtg      96
Ile Ala Gln Tyr Leu Tyr Glu Val Thr Gly Ile Cys Ala Asp Ile Val
                20                  25                  30 acc aac acg gtt acc tat gaa cat ctg cag att gaa caa tac gat gcc     144
Thr Asn Thr Val Thr Tyr Glu His Leu Gln Ile Glu Gln Tyr Asp Ala
            35                  40                  45 gtg gtt ctg tcc ccg ggt ccg ggt cac ccg ggc gaa tat ctg gac ttt     192
Val Val Leu Ser Pro Gly Pro Gly His Pro Gly Glu Tyr Leu Asp Phe
        50                  55                  60 ggc gtc tgc ggt cag gtg atc ctg cat tca ccg gtg ccg ctg ctg ggt     240
Gly Val Cys Gly Gln Val Ile Leu His Ser Pro Val Pro Leu Leu Gly
65                  70                  75 att tgt ctg ggc cac caa ggt atc gcc cag ttc ctg ggc ggt acc gtt     288
Ile Cys Leu Gly His Gln Gly Ile Ala Gln Phe Leu Gly Gly Thr Val
80                  85                  90                  95 ggt cat gca ccg acc ccg gtc cac ggt tat cgt agc aaa att acc cat     336
Gly His Ala Pro Thr Pro Val His Gly Tyr Arg Ser Lys Ile Thr His
                100                 105                 110 agt ggc tcc ggt ctg ttt cgt gat ctg ccg gaa caa ttc gaa gtc gtg     384
Ser Gly Ser Gly Leu Phe Arg Asp Leu Pro Glu Gln Phe Glu Val Val
            115                 120                 125 cgc tac cat tcc ctg atg tgc acc cac ctg ccg cag gaa ctg cgt tgt     432
Arg Tyr His Ser Leu Met Cys Thr His Leu Pro Gln Glu Leu Arg Cys
        130                 135                 140 acg gcc tgg acc gaa gaa ggc gtt gtc atg gca att gaa cac gaa agc     480
Thr Ala Trp Thr Glu Glu Gly Val Val Met Ala Ile Glu His Glu Ser
145                 150                 155 cgc ccg atc tgg ggc gtt cag ttt cat ccg gaa tct atc gat agt gaa     528
Arg Pro Ile Trp Gly Val Gln Phe His Pro Glu Ser Ile Asp Ser Glu
160                 165                 170                 175 tat ggt cac gct ctg ctg tcg aac ttc att ggc atg gcg atc gaa cat     576
Tyr Gly His Ala Leu Leu Ser Asn Phe Ile Gly Met Ala Ile Glu His
                180                 185                 190 aac ggt aat cac cgt acg agc gcg acc cag aac ccg gat gca tca gct     624
Asn Gly Asn His Arg Thr Ser Ala Thr Gln Asn Pro Asp Ala Ser Ala
            195                 200                 205 tcg gcg aat gaa cat tat cgt gct gtg ggc ggt ctg ctg aat atg cag     672
Ser Ala Asn Glu His Tyr Arg Ala Val Gly Gly Leu Leu Asn Met Gln
        210                 215                 220 ctg gcg tat cgc acc tat ccg ggt ccg ttt gac ccg ctg gcc ctg ttc     720
Leu Ala Tyr Arg Thr Tyr Pro Gly Pro Phe Asp Pro Leu Ala Leu Phe
225                 230                 235 acc caa cgc tac gcc cag gat cat cac gca ttt tgg ctg gac tcc gaa     768
Thr Gln Arg Tyr Ala Gln Asp His His Ala Phe Trp Leu Asp Ser Glu
240                 245                 250                 255 aaa tca gaa cgt ccg aac gcc cgc tat tcg att atg ggc agc ggt cag     816
Lys Ser Glu Arg Pro Asn Ala Arg Tyr Ser Ile Met Gly Ser Gly Gln
                260                 265                 270 gca caa ggc tct atc cgt ctg acg tac gat gtg aat agc gaa tct ctg     864
Ala Gln Gly Ser Ile Arg Leu Thr Tyr Asp Val Asn Ser Glu Ser Leu
            275                 280                 285 acc ctg gcg ggc ccg aaa ggt agt cgc att gtc acg ggt gac ttt ttc     912
Thr Leu Ala Gly Pro Lys Gly Ser Arg Ile Val Thr Gly Asp Phe Phe
        290                 295                 300
```

-continued

| | | |
|---|---|---|
| acc ctg ttt tcc caa atc gtg gaa tca gtg aac gtg gcc gtc ccg cag<br>Thr Leu Phe Ser Gln Ile Val Glu Ser Val Asn Val Ala Val Pro Gln<br>305                    310                    315 | 960 |
| tat ctg ccg ttt gaa ttc aaa ggc ggt ttc gtt ggc tat atg ggt tac<br>Tyr Leu Pro Phe Glu Phe Lys Gly Gly Phe Val Gly Tyr Met Gly Tyr<br>320                    325                    330                    335 | 1008 |
| gaa ctg aaa gca ctg acc ggc ggt aat aaa gtg tat cgt agc ggc cag<br>Glu Leu Lys Ala Leu Thr Gly Gly Asn Lys Val Tyr Arg Ser Gly Gln<br>                    340                    345                    350 | 1056 |
| ccg gat gct ggt ttt atg ttc gcg ccg cat ttc ttt gtt ttt gat cat<br>Pro Asp Ala Gly Phe Met Phe Ala Pro His Phe Phe Val Phe Asp His<br>                355                    360                    365 | 1104 |
| cac gac cag acg gtt tac gaa tgc atg att tcg gca acc ggt cag agc<br>His Asp Gln Thr Val Tyr Glu Cys Met Ile Ser Ala Thr Gly Gln Ser<br>            370                    375                    380 | 1152 |
| ccg caa tgg ccg cag ctg ctg acc agc atg acc acg ctg aac aat gct<br>Pro Gln Trp Pro Gln Leu Leu Thr Ser Met Thr Thr Leu Asn Asn Ala<br>385                    390                    395 | 1200 |
| acc gat cgt cgt ccg ttt gtg ccg ggt gcc gtc gat gaa ctg gaa ctg<br>Thr Asp Arg Arg Pro Phe Val Pro Gly Ala Val Asp Glu Leu Glu Leu<br>400                    405                    410                    415 | 1248 |
| agt ctg gaa gac ggt ccg gat gac tac atc cgt aaa gtt aaa caa tcc<br>Ser Leu Glu Asp Gly Pro Asp Asp Tyr Ile Arg Lys Val Lys Gln Ser<br>                    420                    425                    430 | 1296 |
| ctg cag tat att acg gat ggc gaa tca tac gaa atc tgc ctg acc aat<br>Leu Gln Tyr Ile Thr Asp Gly Glu Ser Tyr Glu Ile Cys Leu Thr Asn<br>                435                    440                    445 | 1344 |
| cgt gcg cgc atg agt tat tcc ggt gaa ccg ctg gcc gca tac cgt cgc<br>Arg Ala Arg Met Ser Tyr Ser Gly Glu Pro Leu Ala Ala Tyr Arg Arg<br>            450                    455                    460 | 1392 |
| atg cgt gaa gct agc ccg gtt ccg tat ggc gcg tac ctg tgc ttt gat<br>Met Arg Glu Ala Ser Pro Val Pro Tyr Gly Ala Tyr Leu Cys Phe Asp<br>465                    470                    475 | 1440 |
| tca ttc tcg gtc ctg agc gcg tct ccg gaa acc ttt ctg cgt att gac<br>Ser Phe Ser Val Leu Ser Ala Ser Pro Glu Thr Phe Leu Arg Ile Asp<br>480                    485                    490                    495 | 1488 |
| gaa ggc ggt ctg att gaa tct cgc ccg atc aaa ggt acc cgt gcg cgc<br>Glu Gly Gly Leu Ile Glu Ser Arg Pro Ile Lys Gly Thr Arg Ala Arg<br>                    500                    505                    510 | 1536 |
| tct aaa gat ccg agt gaa gac caa cgt ctg cgc tct gat ctg cag gcc<br>Ser Lys Asp Pro Ser Glu Asp Gln Arg Leu Arg Ser Asp Leu Gln Ala<br>                515                    520                    525 | 1584 |
| agt acc aaa gac cgc gca gaa aac ctg atg att gtc gat ctg gtg cgt<br>Ser Thr Lys Asp Arg Ala Glu Asn Leu Met Ile Val Asp Leu Val Arg<br>            530                    535                    540 | 1632 |
| cat gac ctg aat cag gtg tgc cgc agt ggt tcc gtg cat gtt ccg cac<br>His Asp Leu Asn Gln Val Cys Arg Ser Gly Ser Val His Val Pro His<br>545                    550                    555 | 1680 |
| atc ttt gcc gtc gaa tcg ttc agc tct gtg cat cag ctg gtt agc acg<br>Ile Phe Ala Val Glu Ser Phe Ser Ser Val His Gln Leu Val Ser Thr<br>560                    565                    570                    575 | 1728 |
| gtc cgt ggc cac ctg cgc aac gat att tct acc atg gaa gcc atc cgt<br>Val Arg Gly His Leu Arg Asn Asp Ile Ser Thr Met Glu Ala Ile Arg<br>                    580                    585                    590 | 1776 |
| gca tgc ttt ccg ggc ggt agt atg acg ggt gcc ccg aaa aaa cgt acc<br>Ala Cys Phe Pro Gly Gly Ser Met Thr Gly Ala Pro Lys Lys Arg Thr<br>                595                    600                    605 | 1824 |
| atg gaa att atc gac ggc ctg gaa acc tgt gcc cgc ggt gtt tat tcc<br>Met Glu Ile Ile Asp Gly Leu Glu Thr Cys Ala Arg Gly Val Tyr Ser<br>            610                    615                    620 | 1872 |

```
ggc gca ctg ggt tgg att tca ttt tcg ggc agc gca gaa ctg tca att      1920
Gly Ala Leu Gly Trp Ile Ser Phe Ser Gly Ser Ala Glu Leu Ser Ile
            625                 630                 635 gtg atc cgc acc gct gtt ctg cat aaa cag caa gcg gaa ttc ggt att      1968
Val Ile Arg Thr Ala Val Leu His Lys Gln Gln Ala Glu Phe Gly Ile
640                 645                 650                 655 ggc ggt gct atc gtg gcg cac agc gat ccg aat gaa gaa ctg gaa gaa      2016
Gly Gly Ala Ile Val Ala His Ser Asp Pro Asn Glu Glu Leu Glu Glu
                660                 665                 670 acc ctg gtc aaa gca agc gtg ccg tat tat tcg ttc tat gcc ggt agt      2064
Thr Leu Val Lys Ala Ser Val Pro Tyr Tyr Ser Phe Tyr Ala Gly Ser
            675                 680                 685 gaa aaa tga ctcgag                                                   2079
Glu Lys <210> SEQ ID NO 8
<211> LENGTH: 689
<212> TYPE: PRT
<213> ORGANISM: Artificial Sequence
<220> FEATURE:
<223> OTHER INFORMATION: Pseudomonas fluorescence

<400> SEQUENCE: 8

Met Lys Ile Leu Leu Ile Asp Asn Phe Asp Ser Phe Thr Gln Asn Ile
1               5                   10                  15

Ala Gln Tyr Leu Tyr Glu Val Thr Gly Ile Cys Ala Asp Ile Val Thr
            20                  25                  30

Asn Thr Val Thr Tyr Glu His Leu Gln Ile Glu Gln Tyr Asp Ala Val
        35                  40                  45

Val Leu Ser Pro Gly Pro Gly His Pro Gly Glu Tyr Leu Asp Phe Gly
    50                  55                  60

Val Cys Gly Gln Val Ile Leu His Ser Pro Val Pro Leu Leu Gly Ile
65                  70                  75                  80

Cys Leu Gly His Gln Gly Ile Ala Gln Phe Leu Gly Gly Thr Val Gly
                85                  90                  95

His Ala Pro Thr Pro Val His Gly Tyr Arg Ser Lys Ile Thr His Ser
            100                 105                 110

Gly Ser Gly Leu Phe Arg Asp Leu Pro Glu Gln Phe Glu Val Val Arg
        115                 120                 125

Tyr His Ser Leu Met Cys Thr His Leu Pro Gln Glu Leu Arg Cys Thr
    130                 135                 140

Ala Trp Thr Glu Glu Gly Val Val Met Ala Ile Glu His Glu Ser Arg
145                 150                 155                 160

Pro Ile Trp Gly Val Gln Phe His Pro Glu Ser Ile Asp Ser Glu Tyr
                165                 170                 175

Gly His Ala Leu Leu Ser Asn Phe Ile Gly Met Ala Ile Glu His Asn
            180                 185                 190

Gly Asn His Arg Thr Ser Ala Thr Gln Asn Pro Asp Ala Ser Ala Ser
        195                 200                 205

Ala Asn Glu His Tyr Arg Ala Val Gly Gly Leu Leu Asn Met Gln Leu
    210                 215                 220

Ala Tyr Arg Thr Tyr Pro Gly Pro Phe Asp Pro Leu Ala Leu Phe Thr
225                 230                 235                 240

Gln Arg Tyr Ala Gln Asp His His Ala Phe Trp Leu Asp Ser Glu Lys
                245                 250                 255

Ser Glu Arg Pro Asn Ala Arg Tyr Ser Ile Met Gly Ser Gly Gln Ala
```

-continued

```
                260                 265                 270
Gln Gly Ser Ile Arg Leu Thr Tyr Asp Val Asn Ser Glu Ser Leu Thr
            275                 280                 285
Leu Ala Gly Pro Lys Gly Ser Arg Ile Val Thr Gly Asp Phe Phe Thr
        290                 295                 300
Leu Phe Ser Gln Ile Val Glu Ser Val Asn Val Ala Val Pro Gln Tyr
305                 310                 315                 320
Leu Pro Phe Glu Phe Lys Gly Phe Val Gly Tyr Met Gly Tyr Glu
                325                 330                 335
Leu Lys Ala Leu Thr Gly Gly Asn Lys Val Tyr Arg Ser Gly Gln Pro
            340                 345                 350
Asp Ala Gly Phe Met Phe Ala Pro His Phe Val Phe Asp His His
        355                 360                 365
Asp Gln Thr Val Tyr Glu Cys Met Ile Ser Ala Thr Gly Gln Ser Pro
    370                 375                 380
Gln Trp Pro Gln Leu Leu Thr Ser Met Thr Thr Leu Asn Asn Ala Thr
385                 390                 395                 400
Asp Arg Arg Pro Phe Val Pro Gly Ala Val Asp Glu Leu Glu Leu Ser
                405                 410                 415
Leu Glu Asp Gly Pro Asp Asp Tyr Ile Arg Lys Val Lys Gln Ser Leu
            420                 425                 430
Gln Tyr Ile Thr Asp Gly Glu Ser Tyr Glu Ile Cys Leu Thr Asn Arg
        435                 440                 445
Ala Arg Met Ser Tyr Ser Gly Glu Pro Leu Ala Ala Tyr Arg Arg Met
    450                 455                 460
Arg Glu Ala Ser Pro Val Pro Tyr Gly Ala Tyr Leu Cys Phe Asp Ser
465                 470                 475                 480
Phe Ser Val Leu Ser Ala Ser Pro Glu Thr Phe Leu Arg Ile Asp Glu
                485                 490                 495
Gly Gly Leu Ile Glu Ser Arg Pro Ile Lys Gly Thr Arg Ala Arg Ser
            500                 505                 510
Lys Asp Pro Ser Glu Asp Gln Arg Leu Arg Ser Asp Leu Gln Ala Ser
        515                 520                 525
Thr Lys Asp Arg Ala Glu Asn Leu Met Ile Val Asp Leu Val Arg His
    530                 535                 540
Asp Leu Asn Gln Val Cys Arg Ser Gly Ser Val His Val Pro His Ile
545                 550                 555                 560
Phe Ala Val Glu Ser Phe Ser Ser Val His Gln Leu Val Ser Thr Val
                565                 570                 575
Arg Gly His Leu Arg Asn Asp Ile Ser Thr Met Glu Ala Ile Arg Ala
            580                 585                 590
Cys Phe Pro Gly Gly Ser Met Thr Gly Ala Pro Lys Lys Arg Thr Met
        595                 600                 605
Glu Ile Ile Asp Gly Leu Glu Thr Cys Ala Arg Gly Val Tyr Ser Gly
    610                 615                 620
Ala Leu Gly Trp Ile Ser Phe Ser Gly Ser Ala Glu Leu Ser Ile Val
625                 630                 635                 640
Ile Arg Thr Ala Val Leu His Lys Gln Gln Ala Glu Phe Gly Ile Gly
                645                 650                 655
Gly Ala Ile Val Ala His Ser Asp Pro Asn Glu Glu Leu Glu Glu Thr
            660                 665                 670
Leu Val Lys Ala Ser Val Pro Tyr Tyr Ser Phe Tyr Ala Gly Ser Glu
        675                 680                 685
```

Lys

<210> SEQ ID NO 9
<211> LENGTH: 357
<212> TYPE: DNA
<213> ORGANISM: Artificial Sequence
<220> FEATURE:
<223> OTHER INFORMATION: Pseudomonas fluorescence

<400> SEQUENCE: 9

```
ggatccg atg aat atg acc gaa cac cgc cac atg agc ccg acc acg ccg         49
        Met Asn Met Thr Glu His Arg His Met Ser Pro Thr Thr Pro
        1               5                   10 tct gcc atc ctg caa ccg caa cgc gac caa ctg gac cgt atc aac aac         97
Ser Ala Ile Leu Gln Pro Gln Arg Asp Gln Leu Asp Arg Ile Asn Asn
15                  20                  25                  30 cat ctg gtt gat ctg ctg ggc gaa cgt atg agt gtc tgc atg gat att        145
His Leu Val Asp Leu Leu Gly Glu Arg Met Ser Val Cys Met Asp Ile
                35                  40                  45 gcg gaa ctg aaa gcg gcc cac gac att ccg atg atg cag ccg caa cgt        193
Ala Glu Leu Lys Ala Ala His Asp Ile Pro Met Met Gln Pro Gln Arg
50                  55                  60 atc gtg cag gtt ctg gat caa ctg aaa gac aaa agc tct acc gtg ggt        241
Ile Val Gln Val Leu Asp Gln Leu Lys Asp Lys Ser Ser Thr Val Gly
            65                  70                  75 ctg cgc ccg gac tat gtc cag agc gtg ttt aaa ctg att atc gaa gaa        289
Leu Arg Pro Asp Tyr Val Gln Ser Val Phe Lys Leu Ile Ile Glu Glu
        80                  85                  90 acg tgt atc cag gaa gaa caa ctg att caa cgc cgt cgt aac cag ggt        337
Thr Cys Ile Gln Glu Glu Gln Leu Ile Gln Arg Arg Arg Asn Gln Gly
95                  100                 105                 110 caa cgc tcg tga gcggccgc                                               357
Gln Arg Ser
```

<210> SEQ ID NO 10
<211> LENGTH: 113
<212> TYPE: PRT
<213> ORGANISM: Artificial Sequence
<220> FEATURE:
<223> OTHER INFORMATION: Pseudomonas fluorescence

<400> SEQUENCE: 10

```
Met Asn Met Thr Glu His Arg His Met Ser Pro Thr Thr Pro Ser Ala
1               5                   10                  15

Ile Leu Gln Pro Gln Arg Asp Gln Leu Asp Arg Ile Asn Asn His Leu
            20                  25                  30

Val Asp Leu Leu Gly Glu Arg Met Ser Val Cys Met Asp Ile Ala Glu
        35                  40                  45

Leu Lys Ala Ala His Asp Ile Pro Met Met Gln Pro Gln Arg Ile Val
    50                  55                  60

Gln Val Leu Asp Gln Leu Lys Asp Lys Ser Ser Thr Val Gly Leu Arg
65                  70                  75                  80

Pro Asp Tyr Val Gln Ser Val Phe Lys Leu Ile Ile Glu Glu Thr Cys
                85                  90                  95

Ile Gln Glu Glu Gln Leu Ile Gln Arg Arg Arg Asn Gly Gln Gln Arg
            100                 105                 110

Ser
```

<210> SEQ ID NO 11

```
<211> LENGTH: 28
<212> TYPE: DNA
<213> ORGANISM: Artificial Sequence
<220> FEATURE:
<223> OTHER INFORMATION: Synthesized

<400> SEQUENCE: 11
gacacatatg cgcacgcttc tgatcgac                                   28

<210> SEQ ID NO 12
<211> LENGTH: 28
<212> TYPE: DNA
<213> ORGANISM: Artificial Sequence
<220> FEATURE:
<223> OTHER INFORMATION: Synthesized

<400> SEQUENCE: 12
gacgatatca tcgggcgccc gccacggc                                   28

<210> SEQ ID NO 13
<211> LENGTH: 29
<212> TYPE: DNA
<213> ORGANISM: Artificial Sequence
<220> FEATURE:
<223> OTHER INFORMATION: Synthesized

<400> SEQUENCE: 13
gagccatggg caccgagcag aacgagctg                                  29

<210> SEQ ID NO 14
<211> LENGTH: 30
<212> TYPE: DNA
<213> ORGANISM: Artificial Sequence
<220> FEATURE:
<223> OTHER INFORMATION: Synthesized

<400> SEQUENCE: 14
cagaagcttc accgccggtc ctcggccgtc                                 30

<210> SEQ ID NO 15
<211> LENGTH: 29
<212> TYPE: DNA
<213> ORGANISM: Artificial Sequence
<220> FEATURE:
<223> OTHER INFORMATION: Synthesized

<400> SEQUENCE: 15
cagagacata tgagcggctt cccccgcag                                  29

<210> SEQ ID NO 16
<211> LENGTH: 30
<212> TYPE: DNA
<213> ORGANISM: Artificial Sequence
<220> FEATURE:
<223> OTHER INFORMATION: Synthesized

<400> SEQUENCE: 16
gactcgagtc atcggtcctt ctcgcctttcg                                30

<210> SEQ ID NO 17
<211> LENGTH: 29
<212> TYPE: DNA
<213> ORGANISM: Artificial Sequence
<220> FEATURE:
<223> OTHER INFORMATION: Synthesized

<400> SEQUENCE: 17
```

-continued cagccatggg cacccccgccc gccatcccc    29

<210> SEQ ID NO 18
<211> LENGTH: 28
<212> TYPE: DNA
<213> ORGANISM: Artificial Sequence
<220> FEATURE:
<223> OTHER INFORMATION: Synthesized

<400> SEQUENCE: 18
cagaagcttc acgacacggc ccccgcg    28

<210> SEQ ID NO 19
<211> LENGTH: 31
<212> TYPE: DNA
<213> ORGANISM: Artificial Sequence
<220> FEATURE:
<223> OTHER INFORMATION: Synthesized

<400> SEQUENCE: 19
cagagacata tgagggtgg ttcggtgttc g    31

<210> SEQ ID NO 20
<211> LENGTH: 28
<212> TYPE: DNA
<213> ORGANISM: Artificial Sequence
<220> FEATURE:
<223> OTHER INFORMATION: Synthesized

<400> SEQUENCE: 20
cagatatcag tgcagggcgg tgaacatc    28

<210> SEQ ID NO 21
<211> LENGTH: 25
<212> TYPE: DNA
<213> ORGANISM: Artificial Sequence
<220> FEATURE:
<223> OTHER INFORMATION: Synthesized

<400> SEQUENCE: 21
gagccatggc acctgttaca attga    25

<210> SEQ ID NO 22
<211> LENGTH: 33
<212> TYPE: DNA
<213> ORGANISM: Artificial Sequence
<220> FEATURE:
<223> OTHER INFORMATION: Synthesized

<400> SEQUENCE: 22
gacggatcct attttttatt tcttttaaag tgc    33

<210> SEQ ID NO 23
<211> LENGTH: 1922
<212> TYPE: DNA
<213> ORGANISM: Artificial Sequence
<220> FEATURE:
<223> OTHER INFORMATION: E. coli

<400> SEQUENCE: 23 gagcc atg gca cct gtt aca att gaa aag ttc gta aat caa gaa gaa cga    50
      Met Ala Pro Val Thr Ile Glu Lys Phe Val Asn Gln Glu Glu Arg
      1               5                  10                  15 cac ctt gtt tcc aac cga tca gca aca att ccg ttt ggt gaa tac ata    98
His Leu Val Ser Asn Arg Ser Ala Thr Ile Pro Phe Gly Glu Tyr Ile -continued

|  |  | 20 |  |  |  | 25 |  |  |  | 30 |  |  |  |  |
|---|---|---|---|---|---|---|---|---|---|---|---|---|---|---|
| ttt | aaa | aga | ttg | ttg | tcc | atc | gat | acg | aaa | tca | gtt | ttc | ggt | gtt | cct | 146 |
| Phe | Lys | Arg | Leu | Leu | Ser | Ile | Asp | Thr | Lys | Ser | Val | Phe | Gly | Val | Pro |  |
|  |  | 35 |  |  |  | 40 |  |  |  | 45 |  |  |  |  |

```
ggt gac ttc aac tta tct cta tta gaa tat ctc tat tca cct agt gtt      194
Gly Asp Phe Asn Leu Ser Leu Leu Glu Tyr Leu Tyr Ser Pro Ser Val
         50                  55                  60 gaa tca gct ggc cta aga tgg gtc ggc acg tgt aat gaa ctg aac gcc      242
Glu Ser Ala Gly Leu Arg Trp Val Gly Thr Cys Asn Glu Leu Asn Ala
 65                  70                  75 gct tat gcg gcc gac gga tat tcc cgt tac tct aat aag att ggc tgt      290
Ala Tyr Ala Ala Asp Gly Tyr Ser Arg Tyr Ser Asn Lys Ile Gly Cys
 80                  85                  90                  95 tta ata acc acg tat ggc gtt ggt gaa tta agc gcc ttg aac ggt ata      338
Leu Ile Thr Thr Tyr Gly Val Gly Glu Leu Ser Ala Leu Asn Gly Ile
         100                 105                 110 gcc ggt tcg ttc gct gaa aat gtc aaa gtt ttg cac att gtt ggt gtg      386
Ala Gly Ser Phe Ala Glu Asn Val Lys Val Leu His Ile Val Gly Val
         115                 120                 125 gcc aag tcc ata gat tcg cgt tca agt aac ttt agt gat cgg aac cta      434
Ala Lys Ser Ile Asp Ser Arg Ser Ser Asn Phe Ser Asp Arg Asn Leu
         130                 135                 140 cat cat ttg gtc cca cag cta cat gat tca aat ttt aaa ggg cca aat      482
His His Leu Val Pro Gln Leu His Asp Ser Asn Phe Lys Gly Pro Asn
 145                 150                 155 cat aaa gta tat cat gat atg gta aaa gat aga gtc gct tgc tcg gta      530
His Lys Val Tyr His Asp Met Val Lys Asp Arg Val Ala Cys Ser Val
 160                 165                 170                 175 gcc tac ttg gag gat att gaa act gca tgt gac caa gtc gat aat gtt      578
Ala Tyr Leu Glu Asp Ile Glu Thr Ala Cys Asp Gln Val Asp Asn Val
         180                 185                 190 atc cgc gat att tac aag tat tct aaa cct ggt tat att ttt gtt cct      626
Ile Arg Asp Ile Tyr Lys Tyr Ser Lys Pro Gly Tyr Ile Phe Val Pro
         195                 200                 205 gca gat ttt gcg gat atg tct gtt aca tgt gat aat ttg gtt aat gtt      674
Ala Asp Phe Ala Asp Met Ser Val Thr Cys Asp Asn Leu Val Asn Val
         210                 215                 220 cca cgt ata tct caa caa gat tgt ata gta tac cct tct gaa aac caa      722
Pro Arg Ile Ser Gln Gln Asp Cys Ile Val Tyr Pro Ser Glu Asn Gln
 225                 230                 235 ttg tct gac ata atc aac aag att act agt tgg ata tat tcc agt aaa      770
Leu Ser Asp Ile Ile Asn Lys Ile Thr Ser Trp Ile Tyr Ser Ser Lys
 240                 245                 250                 255 aca cct gcg atc ctt gga gac gta ctg act gat agg tat ggt gtg agt      818
Thr Pro Ala Ile Leu Gly Asp Val Leu Thr Asp Arg Tyr Gly Val Ser
         260                 265                 270 aac ttt ttg aac aag ctt atc tgc aaa act ggg att tgg aat ttt tcc      866
Asn Phe Leu Asn Lys Leu Ile Cys Lys Thr Gly Ile Trp Asn Phe Ser
         275                 280                 285 act gtt atg gga aaa tct gta att gat gag tca aac cca act tat atg      914
Thr Val Met Gly Lys Ser Val Ile Asp Glu Ser Asn Pro Thr Tyr Met
         290                 295                 300 ggt caa tat aat ggt aaa gaa ggt tta aaa caa gtc tat gaa cat ttt      962
Gly Gln Tyr Asn Gly Lys Glu Gly Leu Lys Gln Val Tyr Glu His Phe
 305                 310                 315 gaa ctg tgc gac ttg gtc ttg cat ttt gga gtc gac atc aat gaa att     1010
Glu Leu Cys Asp Leu Val Leu His Phe Gly Val Asp Ile Asn Glu Ile
 320                 325                 330                 335 aat aat ggg cat tat act ttt act tat aaa cca aat gct aaa atc att     1058
```

|  |  |
|---|---|
| Asn Asn Gly His Tyr Thr Phe Thr Tyr Lys Pro Asn Ala Lys Ile Ile<br>                340                        345                  350 |  |
| caa ttt cat ccg aat tat att cgc ctt gtg gac act agg cag ggc aat<br>Gln Phe His Pro Asn Tyr Ile Arg Leu Val Asp Thr Arg Gln Gly Asn<br>          355                        360                  365 | 1106 |
| gag caa atg ttc aaa gga atc aat ttt gcc cct att tta aaa gaa cta<br>Glu Gln Met Phe Lys Gly Ile Asn Phe Ala Pro Ile Leu Lys Glu Leu<br>                370                        375                  380 | 1154 |
| tac aag cgc att gac gtt tct aaa ctt tct ttg caa tat gat tca aat<br>Tyr Lys Arg Ile Asp Val Ser Lys Leu Ser Leu Gln Tyr Asp Ser Asn<br>385                      390                        395 | 1202 |
| gta act caa tat acg aac gaa aca atg cgg tta gaa gat cct acc aat<br>Val Thr Gln Tyr Thr Asn Glu Thr Met Arg Leu Glu Asp Pro Thr Asn<br>400                      405                        410                  415 | 1250 |
| gga caa tca agc att att aca caa gtt cac tta caa aag acg atg cct<br>Gly Gln Ser Ser Ile Ile Thr Gln Val His Leu Gln Lys Thr Met Pro<br>                420                        425                  430 | 1298 |
| aaa ttt ttg aac cct ggt gat gtc gtt tgt gaa aca ggc tct ttt<br>Lys Phe Leu Asn Pro Gly Asp Val Val Val Cys Glu Thr Gly Ser Phe<br>                    435                        440                  445 | 1346 |
| caa ttc tct gtt cgt gat ttc gcg ttt cct tcg caa tta aaa tat ata<br>Gln Phe Ser Val Arg Asp Phe Ala Phe Pro Ser Gln Leu Lys Tyr Ile<br>          450                        455                  460 | 1394 |
| tcg caa gga ttt ttc ctt tcc att ggc atg gcc ctt cct gcc gcc cta<br>Ser Gln Gly Phe Phe Leu Ser Ile Gly Met Ala Leu Pro Ala Ala Leu<br>465                      470                        475 | 1442 |
| ggt gtt gga att gcc atg caa gac cac tca aac gct cac atc aat ggt<br>Gly Val Gly Ile Ala Met Gln Asp His Ser Asn Ala His Ile Asn Gly<br>480                      485                        490                  495 | 1490 |
| ggc aac gta aaa gag gac tat aag cca aga tta att ttg ttt gaa ggt<br>Gly Asn Val Lys Glu Asp Tyr Lys Pro Arg Leu Ile Leu Phe Glu Gly<br>                500                        505                  510 | 1538 |
| gac ggt gca gca cag atg aca atc caa gaa ctg agc acc att ctg aag<br>Asp Gly Ala Ala Gln Met Thr Ile Gln Glu Leu Ser Thr Ile Leu Lys<br>                515                        520                  525 | 1586 |
| tgc aat att cca cta gaa gtt atc att tgg aac aat aac ggc tac act<br>Cys Asn Ile Pro Leu Glu Val Ile Ile Trp Asn Asn Asn Gly Tyr Thr<br>          530                        535                  540 | 1634 |
| att gaa aga gcc atc atg ggc cct acc agg tcg tat aac gac gtt atg<br>Ile Glu Arg Ala Ile Met Gly Pro Thr Arg Ser Tyr Asn Asp Val Met<br>545                      550                        555 | 1682 |
| tct tgg aaa tgg acc aaa cta ttt gaa gca ttc gga gac ttc gac gga<br>Ser Trp Lys Trp Thr Lys Leu Phe Glu Ala Phe Gly Asp Phe Asp Gly<br>560                      565                        570                  575 | 1730 |
| aag tat act aat agc act ctc att caa tgt ccc tct aaa tta gca ctg<br>Lys Tyr Thr Asn Ser Thr Leu Ile Gln Cys Pro Ser Lys Leu Ala Leu<br>                580                        585                  590 | 1778 |
| aaa ttg gag gag ctt aag aat tca aac aaa aga agc ggg ata gaa ctt<br>Lys Leu Glu Glu Leu Lys Asn Ser Asn Lys Arg Ser Gly Ile Glu Leu<br>595                      600                        605 | 1826 |
| tta gaa gtc aaa tta ggc gaa ttg gat ttc ccc gaa cag cta aag tgc<br>Leu Glu Val Lys Leu Gly Glu Leu Asp Phe Pro Glu Gln Leu Lys Cys<br>          610                        615                  620 | 1874 |
| atg gtt gaa gca gcg gca ctt aaa aga aat aaa aaa tag ggatccgtc<br>Met Val Glu Ala Ala Ala Leu Lys Arg Asn Lys Lys<br>625                      630                        635 | 1922 |

<210> SEQ ID NO 24
<211> LENGTH: 635
<212> TYPE: PRT

<213> ORGANISM: Artificial Sequence
<220> FEATURE:
<223> OTHER INFORMATION: E. coli

<400> SEQUENCE: 24

```
Met Ala Pro Val Thr Ile Glu Lys Phe Val Asn Gln Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
    210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
    290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
    370                 375                 380

Lys Arg Ile Asp Val Ser Lys Leu Ser Leu Gln Tyr Asp Ser Asn Val
```

```
                385                 390                 395                 400
        Thr Gln Tyr Thr Asn Glu Thr Met Arg Leu Glu Asp Pro Thr Asn Gly
                        405                 410                 415
        Gln Ser Ser Ile Ile Thr Gln Val His Leu Gln Lys Thr Met Pro Lys
                        420                 425                 430
        Phe Leu Asn Pro Gly Asp Val Val Cys Glu Thr Gly Ser Phe Gln
                    435                 440                 445
        Phe Ser Val Arg Asp Phe Ala Phe Pro Ser Gln Leu Lys Tyr Ile Ser
        450                 455                 460
        Gln Gly Phe Phe Leu Ser Ile Gly Met Ala Leu Pro Ala Ala Leu Gly
        465                 470                 475                 480
        Val Gly Ile Ala Met Gln Asp His Ser Asn Ala His Ile Asn Gly Gly
                        485                 490                 495
        Asn Val Lys Glu Asp Tyr Lys Pro Arg Leu Ile Leu Phe Glu Gly Asp
                        500                 505                 510
        Gly Ala Ala Gln Met Thr Ile Gln Glu Leu Ser Thr Ile Leu Lys Cys
                    515                 520                 525
        Asn Ile Pro Leu Glu Val Ile Ile Trp Asn Asn Gly Tyr Thr Ile
                530                 535                 540
        Glu Arg Ala Ile Met Gly Pro Thr Arg Ser Tyr Asn Asp Val Met Ser
        545                 550                 555                 560
        Trp Lys Trp Thr Lys Leu Phe Glu Ala Phe Gly Asp Phe Asp Gly Lys
                        565                 570                 575
        Tyr Thr Asn Ser Thr Leu Ile Gln Cys Pro Ser Lys Leu Ala Leu Lys
                    580                 585                 590
        Leu Glu Glu Leu Lys Asn Ser Asn Lys Arg Ser Gly Ile Glu Leu Leu
                    595                 600                 605
        Glu Val Lys Leu Gly Glu Leu Asp Phe Pro Glu Gln Leu Lys Cys Met
                610                 615                 620
        Val Glu Ala Ala Ala Leu Lys Arg Asn Lys Lys
        625                 630                 635

<210> SEQ ID NO 25
<211> LENGTH: 30
<212> TYPE: DNA
<213> ORGANISM: Artificial Sequence
<220> FEATURE:
<223> OTHER INFORMATION: Synthesized

<400> SEQUENCE: 25
gacggatccg atggcccct ccgtcgactc                                         30

<210> SEQ ID NO 26
<211> LENGTH: 30
<212> TYPE: DNA
<213> ORGANISM: Artificial Sequence
<220> FEATURE:
<223> OTHER INFORMATION: Synthesized

<400> SEQUENCE: 26
gctgaattct tatgccatca tcttgacgag                                        30

<210> SEQ ID NO 27
<211> LENGTH: 2121
<212> TYPE: DNA
<213> ORGANISM: Artificial Sequence
<220> FEATURE:
<223> OTHER INFORMATION: Yeast Rhodotorula glutinis
```

-continued

```
<400> SEQUENCE: 27 atg gcc ccc tcc gtc gac tcg atc gcg act tcg gtc gcc aac tcg ctc      48
Met Ala Pro Ser Val Asp Ser Ile Ala Thr Ser Val Ala Asn Ser Leu
1               5                   10                  15 tcg aac gga ctc gcc ggc gac ctc cgc aag aag act tcg ggt gct ggc      96
Ser Asn Gly Leu Ala Gly Asp Leu Arg Lys Lys Thr Ser Gly Ala Gly
            20                  25                  30 tcc ctg ctg ccg acc acc gag act acc cag atc gac atc gtc gag cgc     144
Ser Leu Leu Pro Thr Thr Glu Thr Thr Gln Ile Asp Ile Val Glu Arg
        35                  40                  45 atc ttg gcc gac gcc ggc gcg acg gac cag atc aaa ctc gac ggg tat     192
Ile Leu Ala Asp Ala Gly Ala Thr Asp Gln Ile Lys Leu Asp Gly Tyr
    50                  55                  60 acc ctc acc ctc ggc gac gtc gtc ggc gcc gcc cgc cgc ggc cgc acc     240
Thr Leu Thr Leu Gly Asp Val Val Gly Ala Ala Arg Arg Gly Arg Thr
65                  70                  75                  80 gtc aag gtc gcc gat agc ccc cag att cgc gag aag atc gat gcc agt     288
Val Lys Val Ala Asp Ser Pro Gln Ile Arg Glu Lys Ile Asp Ala Ser
                85                  90                  95 gtc gag ttc ctc cgc acc cag ctt gac aac agt gtc tac ggt gtc acg     336
Val Glu Phe Leu Arg Thr Gln Leu Asp Asn Ser Val Tyr Gly Val Thr
            100                 105                 110 acc ggc ttc ggc ggc tcg gca gac acc cgg acg gag gac gcg atc tcg     384
Thr Gly Phe Gly Gly Ser Ala Asp Thr Arg Thr Glu Asp Ala Ile Ser
        115                 120                 125 ctg cag aag gct ctg ctc gag cac caa ctc tgc ggt gtc ctg ccc acc     432
Leu Gln Lys Ala Leu Leu Glu His Gln Leu Cys Gly Val Leu Pro Thr
    130                 135                 140 tcg atg gac ggg ttc gcg ctc gga cgt ggc ctc gag aac tcg ctc ccg     480
Ser Met Asp Gly Phe Ala Leu Gly Arg Gly Leu Glu Asn Ser Leu Pro
145                 150                 155                 160 ctc gag gtt gtt cgt ggc gcg atg acg atc cgt gtc aac tcg ctc acg     528
Leu Glu Val Val Arg Gly Ala Met Thr Ile Arg Val Asn Ser Leu Thr
                165                 170                 175 cgc ggc cac tcg gcg gtc cgc atc gtc gtc ctc gaa gcc ctc acc aac     576
Arg Gly His Ser Ala Val Arg Ile Val Val Leu Glu Ala Leu Thr Asn
            180                 185                 190 ttc ctc aac cac ggc atc acc ccg atc gtc ccc ctc cgc ggc acc atc     624
Phe Leu Asn His Gly Ile Thr Pro Ile Val Pro Leu Arg Gly Thr Ile
        195                 200                 205 tcg gca tcg ggt gac ctt tcc ccc ctc tcg tac atc gcc gcc tcg atc     672
Ser Ala Ser Gly Asp Leu Ser Pro Leu Ser Tyr Ile Ala Ala Ser Ile
    210                 215                 220 acc ggt cac cca gac tcg aag gtg cac gtc gac ggc caa atc atg tcc     720
Thr Gly His Pro Asp Ser Lys Val His Val Asp Gly Gln Ile Met Ser
225                 230                 235                 240 gcc cag gag gcg atc gct ctc aag ggt ctc caa cct gtc gtc ctc ggt     768
Ala Gln Glu Ala Ile Ala Leu Lys Gly Leu Gln Pro Val Val Leu Gly
                245                 250                 255 ccg aag gag ggt ctc ggg ctc gtc aac ggc acc gcc gtc tcc gcg tcc     816
Pro Lys Glu Gly Leu Gly Leu Val Asn Gly Thr Ala Val Ser Ala Ser
            260                 265                 270 atg gcc act ctc gcc ctc acc gac gcg cat gtc ctc tcg ttg ctc gcc     864
Met Ala Thr Leu Ala Leu Thr Asp Ala His Val Leu Ser Leu Leu Ala
        275                 280                 285 cag gcc aac acg gcc ctg acc gtc gag gcc atg gtc gga cac gcc ggc     912
Gln Ala Asn Thr Ala Leu Thr Val Glu Ala Met Val Gly His Ala Gly
    290                 295                 300 tcg ttc cac ccg ttc ctg cac gat gtc act cgc ccg cac ccg acc cag     960
```

```
Ser Phe His Pro Phe Leu His Asp Val Thr Arg Pro His Pro Thr Gln
305                 310                 315                 320 atc gag gtc gcg cgc aac att agg acg ctc ctc gag ggc agc aag tac        1008
Ile Glu Val Ala Arg Asn Ile Arg Thr Leu Leu Glu Gly Ser Lys Tyr
                        325                 330                 335 gcc gtc cac cat gag acc gag gtc aag gtc aag gac gac gag ggc atc        1056
Ala Val His His Glu Thr Glu Val Lys Val Lys Asp Asp Glu Gly Ile
                340                 345                 350 ctc cgg cag gac cga tac ccg ctc cgc tgc tcg ccc cag tgg ctc ggg        1104
Leu Arg Gln Asp Arg Tyr Pro Leu Arg Cys Ser Pro Gln Trp Leu Gly
            355                 360                 365 cct ctt gtc agt gac atg atc cac gcc cac tcg gtc ctc tcc ctc gag        1152
Pro Leu Val Ser Asp Met Ile His Ala His Ser Val Leu Ser Leu Glu
        370                 375                 380 gcg ggt cag tcg acc acc gac aac ccc ctg atc gac ctc gag aac aag        1200
Ala Gly Gln Ser Thr Thr Asp Asn Pro Leu Ile Asp Leu Glu Asn Lys
385                 390                 395                 400 atg acc cac cac ggt ggc gcc ttc atg gcg agc agc gtc ggt aac acc        1248
Met Thr His His Gly Gly Ala Phe Met Ala Ser Ser Val Gly Asn Thr
                    405                 410                 415 atg gag aag act cgt ctc gcc gtc gca ctt atg ggc aag gtt agc ttc        1296
Met Glu Lys Thr Arg Leu Ala Val Ala Leu Met Gly Lys Val Ser Phe
                420                 425                 430 act cag ctc acc gag atg ctc aac gcc ggc atg aac cgc gcg ctt ccc        1344
Thr Gln Leu Thr Glu Met Leu Asn Ala Gly Met Asn Arg Ala Leu Pro
            435                 440                 445 tcc tgc ctc gcc gcc gag gac ccg tct ctg tcc tac cac tgc aag ggt        1392
Ser Cys Leu Ala Ala Glu Asp Pro Ser Leu Ser Tyr His Cys Lys Gly
450                 455                 460 ctc gac atc gcc gcc gct gca tac act tcg gag ctc ggt cac ctc gcg        1440
Leu Asp Ile Ala Ala Ala Ala Tyr Thr Ser Glu Leu Gly His Leu Ala
465                 470                 475                 480 aac cca gtc tcg acc cac gtt cag ccg gca gag atg ggc aat cag gcg        1488
Asn Pro Val Ser Thr His Val Gln Pro Ala Glu Met Gly Asn Gln Ala
                    485                 490                 495 atc aac tcg ctc gcc ctc atc tcg gcc cgt cgc acc gcc gag gcg aac        1536
Ile Asn Ser Leu Ala Leu Ile Ser Ala Arg Arg Thr Ala Glu Ala Asn
                500                 505                 510 gac gtc ctc tcg ctc ctc ctc gcc acc cac ctc tac tgc gtc ttg cag        1584
Asp Val Leu Ser Leu Leu Leu Ala Thr His Leu Tyr Cys Val Leu Gln
            515                 520                 525 gcg gtc gac ctg cgc gcg atg gag ttc gag cac acg aaa gag ttt gag        1632
Ala Val Asp Leu Arg Ala Met Glu Phe Glu His Thr Lys Glu Phe Glu
        530                 535                 540 ccg atg gtc acc gac ttg ctc aag cag cac ttt ggc gcg ctc gcg aca        1680
Pro Met Val Thr Asp Leu Leu Lys Gln His Phe Gly Ala Leu Ala Thr
545                 550                 555                 560 gcc gac gtc gag gac aag gtc cgc aaa tcg atc tac aag cgg ctg cag        1728
Ala Asp Val Glu Asp Lys Val Arg Lys Ser Ile Tyr Lys Arg Leu Gln
                    565                 570                 575 cag aac aac tcg tac gac ctc gag cag cgg tgg cac gac acg ttc tcg        1776
Gln Asn Asn Ser Tyr Asp Leu Glu Gln Arg Trp His Asp Thr Phe Ser
                580                 585                 590 gtc gcg acc ggc gcc gtc gtc gaa gcc ctc gcc ggg aac gag gtg tcg        1824
Val Ala Thr Gly Ala Val Val Glu Ala Leu Ala Gly Asn Glu Val Ser
            595                 600                 605 ctc gcg agc ctg aac gcc tgg aag gtc gcg tgc gct gag aag gcc atc        1872
Leu Ala Ser Leu Asn Ala Trp Lys Val Ala Cys Ala Glu Lys Ala Ile
        610                 615                 620
```

```
gcc ctg acc cgc acc gtg cgc gac tcg ttc tgg gcc gcg ccg tcg tcg        1920
Ala Leu Thr Arg Thr Val Arg Asp Ser Phe Trp Ala Ala Pro Ser Ser
625                 630                 635                 640 gcg tcg ccc gcg ctc aag tac ctc tcg ccg cgg act cgc atc ctg tac        1968
Ala Ser Pro Ala Leu Lys Tyr Leu Ser Pro Arg Thr Arg Ile Leu Tyr
                645                 650                 655 tcg ttc gtc cgg gaa gac gtc ggc gtc aag gcc cgc cgc ggc gac gtc        2016
Ser Phe Val Arg Glu Asp Val Gly Val Lys Ala Arg Arg Gly Asp Val
            660                 665                 670 tac ctc ggc aag cag gag gtc acg atc ggg acc aac gtc agc cgc atc        2064
Tyr Leu Gly Lys Gln Glu Val Thr Ile Gly Thr Asn Val Ser Arg Ile
        675                 680                 685 tac gag gcg atc aag gac ggc cgc att gct ccg gtc ctc gtc aag atg        2112
Tyr Glu Ala Ile Lys Asp Gly Arg Ile Ala Pro Val Leu Val Lys Met
    690                 695                 700 atg gca taa                                                            2121
Met Ala
705

<210> SEQ ID NO 28
<211> LENGTH: 706
<212> TYPE: PRT
<213> ORGANISM: Artificial Sequence
<220> FEATURE:
<223> OTHER INFORMATION: Yeast Rhodotorula glutinis

<400> SEQUENCE: 28

Met Ala Pro Ser Val Asp Ser Ile Ala Thr Ser Val Ala Asn Ser Leu
1               5                   10                  15

Ser Asn Gly Leu Ala Gly Asp Leu Arg Lys Lys Thr Ser Gly Ala Gly
            20                  25                  30

Ser Leu Leu Pro Thr Thr Glu Thr Thr Gln Ile Asp Ile Val Glu Arg
        35                  40                  45

Ile Leu Ala Asp Ala Gly Ala Thr Asp Gln Ile Lys Leu Asp Gly Tyr
    50                  55                  60

Thr Leu Thr Leu Gly Asp Val Val Gly Ala Ala Arg Arg Gly Arg Thr
65                  70                  75                  80

Val Lys Val Ala Asp Ser Pro Gln Ile Arg Glu Lys Ile Asp Ala Ser
                85                  90                  95

Val Glu Phe Leu Arg Thr Gln Leu Asp Asn Ser Val Tyr Gly Val Thr
            100                 105                 110

Thr Gly Phe Gly Gly Ser Ala Asp Thr Arg Thr Glu Asp Ala Ile Ser
        115                 120                 125

Leu Gln Lys Ala Leu Leu Glu His Gln Leu Cys Gly Val Leu Pro Thr
    130                 135                 140

Ser Met Asp Gly Phe Ala Leu Gly Arg Gly Leu Glu Asn Ser Leu Pro
145                 150                 155                 160

Leu Glu Val Val Arg Gly Ala Met Thr Ile Arg Val Asn Ser Leu Thr
                165                 170                 175

Arg Gly His Ser Ala Val Arg Ile Val Leu Glu Ala Leu Thr Asn
            180                 185                 190

Phe Leu Asn His Gly Ile Thr Pro Ile Val Pro Leu Arg Gly Thr Ile
        195                 200                 205

Ser Ala Ser Gly Asp Leu Ser Pro Leu Ser Tyr Ile Ala Ala Ser Ile
    210                 215                 220

Thr Gly His Pro Asp Ser Lys Val His Val Asp Gly Gln Ile Met Ser
225                 230                 235                 240
```

```
Ala Gln Glu Ala Ile Ala Leu Lys Gly Leu Gln Pro Val Val Leu Gly
                245                 250                 255

Pro Lys Glu Gly Leu Gly Leu Val Asn Gly Thr Ala Val Ser Ala Ser
            260                 265                 270

Met Ala Thr Leu Ala Leu Thr Asp Ala His Val Leu Ser Leu Leu Ala
        275                 280                 285

Gln Ala Asn Thr Ala Leu Thr Val Glu Ala Met Val Gly His Ala Gly
    290                 295                 300

Ser Phe His Pro Phe Leu His Asp Val Thr Arg Pro His Pro Thr Gln
305                 310                 315                 320

Ile Glu Val Ala Arg Asn Ile Arg Thr Leu Leu Glu Gly Ser Lys Tyr
                325                 330                 335

Ala Val His His Glu Thr Glu Val Lys Val Lys Asp Asp Glu Gly Ile
            340                 345                 350

Leu Arg Gln Asp Arg Tyr Pro Leu Arg Cys Ser Pro Gln Trp Leu Gly
        355                 360                 365

Pro Leu Val Ser Asp Met Ile His Ala His Ser Val Leu Ser Leu Glu
    370                 375                 380

Ala Gly Gln Ser Thr Thr Asp Asn Pro Leu Ile Asp Leu Glu Asn Lys
385                 390                 395                 400

Met Thr His His Gly Gly Ala Phe Met Ala Ser Ser Val Gly Asn Thr
                405                 410                 415

Met Glu Lys Thr Arg Leu Ala Val Ala Leu Met Gly Lys Val Ser Phe
            420                 425                 430

Thr Gln Leu Thr Glu Met Leu Asn Ala Gly Met Asn Arg Ala Leu Pro
        435                 440                 445

Ser Cys Leu Ala Ala Glu Asp Pro Ser Leu Ser Tyr His Cys Lys Gly
    450                 455                 460

Leu Asp Ile Ala Ala Ala Tyr Thr Ser Glu Leu Gly His Leu Ala
465                 470                 475             480

Asn Pro Val Ser Thr His Val Gln Pro Ala Glu Met Gly Asn Gln Ala
                485                 490                 495

Ile Asn Ser Leu Ala Leu Ile Ser Ala Arg Arg Thr Ala Glu Ala Asn
            500                 505                 510

Asp Val Leu Ser Leu Leu Ala Thr His Leu Tyr Cys Val Leu Gln
        515                 520                 525

Ala Val Asp Leu Arg Ala Met Glu Phe Glu His Thr Lys Glu Phe Glu
    530                 535                 540

Pro Met Val Thr Asp Leu Leu Lys Gln His Phe Gly Ala Leu Ala Thr
545                 550                 555                 560

Ala Asp Val Glu Asp Lys Val Arg Lys Ser Ile Tyr Lys Arg Leu Gln
                565                 570                 575

Gln Asn Asn Ser Tyr Asp Leu Glu Gln Arg Trp His Asp Thr Phe Ser
            580                 585                 590

Val Ala Thr Gly Ala Val Val Glu Ala Leu Ala Gly Asn Glu Val Ser
        595                 600                 605

Leu Ala Ser Leu Asn Ala Trp Lys Val Ala Cys Ala Glu Lys Ala Ile
    610                 615                 620

Ala Leu Thr Arg Thr Val Arg Asp Ser Phe Trp Ala Ala Pro Ser Ser
625                 630                 635                 640

Ala Ser Pro Ala Leu Lys Tyr Leu Ser Pro Arg Thr Arg Ile Leu Tyr
                645                 650                 655

Ser Phe Val Arg Glu Asp Val Gly Val Lys Ala Arg Arg Gly Asp Val
```

```
                    660                 665                 670
Tyr Leu Gly Lys Gln Glu Val Thr Ile Gly Thr Asn Val Ser Arg Ile
                675                 680                 685

Tyr Glu Ala Ile Lys Asp Gly Arg Ile Ala Pro Val Leu Val Lys Met
        690                 695                 700

Met Ala
705
```

METHOD FOR PRODUCING ANILINE DERIVATIVE BY FERMENTATION FROM CARBON SOURCE

This application is a continuation of PCT/JP2015/058295, filed Mar. 19, 2015, which claims priority of JP2014-058570, filed Mar. 20, 2014. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Sep. 9, 2016, and a size of 62.0 kilobytes. The Sequence Listing filed via EFS-Web is part of the specification and is hereby incorporated in its entirety by reference herein.

TECHNICAL FIELD

The present invention relates to a method for producing an aniline derivative by fermentation from a carbon source. More specifically, the invention relates to a method for producing at least one aniline derivative selected from the group consisting of 4-aminophenylalanine (4APhe), 4-aminocinnamic acid (4ACA), 2-(4-aminophenyl)aldehyde, 4-aminophenylacetic acid and 4-aminophenethylethanol (4APE), from a carbon source such as glucose, by creating a microorganism imparted with the function of biosynthesizing 4-aminophenylpyruvic acid from chorismic acid, using a genetic engineering method, and conducting fermentation using the microorganism.

BACKGROUND ART

In recent years, in response to the problem of global warming caused by petroleum-derived carbon dioxide, opportunities continue to arise throughout the world to overhaul social structures that are overdependent on fossil fuels. This trend is leading to increasingly active operation of "biorefineries" that make use of bioprocessing technology, for which research is accelerating throughout the world, but unfortunately under the current state of affairs no research results have yet been obtained for biosynthesis of aromatic compounds, although in light of the importance of aromatic compounds including aniline derivatives for the chemical industry, diligent efforts are being expended in research toward synthesis of aromatic polymers.

For example, PTL 1 discloses a technique relating to polymer synthesis using 4-aminocinnamic acid (4ACA) which is a natural molecule, and reports that a high heat-proof polymer is obtained from 4-aminocinnamic acid.

Also, as disclosed in NPL 1, the metabolic pathway for biosynthesis of 4-aminophenylalanine (4APhe) via shikimic acid has been elucidated (see p. 2818, FIG. 1), but there has been no disclosure nor teaching of ammonia-lyase functioning in an organism and converting 4-aminophenylalanine to 4-aminocinnamic acid.

NPL 2 describes isolation of the gene for phenylalanine ammonia-lyase of the yeast *Rhodotorula glutinis* JN-1 (hereunder abbreviated as "Rgpal"), depositing of the yeast at CCTCC (China Center For Type Culture Collection) as deposit number M2011490, and creation of an optimum pH mutant by site-specific mutagenesis of the gene. Furthermore, since the Chinese Patent Application specification of which the authors of NPL 2 are the inventors (hereunder, PTL 2) was published on Apr. 24, 2013, the actual sequence of Rgpal is publicly known. However, it is not disclosed that the enzyme can produce 4-aminocinnamic acid using 4-aminophenylalanine as the substrate.

Thus, 4-aminophenylalanine (4APhe) is an important substance in that it is a precursor for 4-aminocinnamic acid (4ACA).

Also, NPL 3 discloses, as shown in FIG. 1, conversion of chorismic acid to 4-amino-4-deoxychorismic acid (ADC) by PapA (4-amino-4-deoxychorismic acid synthase), conversion of ADC to 4-amino-4-deoxyprephenate (ADP) by PapB (4-amino-4-deoxychorismic acid mutase), and conversion of ADP to 4-aminophenylpyruvic acid by PapC (4-amino-4-deoxyprephenate dehydrogenase).

Also, it is believed that 4-aminophenylpyruvic acid is converted to 4-aminophenylalanine (4APhe) by the action of microbial endogenous enzymes.

In addition, PTL 3 discloses that biosynthesis of 4-amino-4-deoxychorismic acid (ADC), at least catalyzed by an enzyme belonging to the class of aminodeoxychorismic acid synthases, is carried out by in vivo fermentation in a host microorganism having 4-amino-4-deoxychorismic acid synthase at an increased level of activity, while obtaining a fermentation culture broth comprising 4-amino-4-deoxychorismic acid (ADC) and 4-amino-4-deoxyprephenate (ADP), and that the compounds are recovered from the fermentation culture broth, either together or each one separately.

However, when the conventionally known pap genes, i.e. the 3 key enzymes known in pathways of antibiotic production (for example, PapA, PapB, PapC of *Streptomyces venezuelae*) are simply utilized directly, the productivity of 4-aminophenylalanine (4APhe) by fermentation is no more than about 0.2 g/L, and even attempting various combinations of conventionally known pap genes, it accumulates at no more than about 0.9 g/L.

Such low productivity has been an obstacle when trying achieve industrial mass production of aniline derivatives including 4-aminophenylalanine (4APhe), 4-aminocinnamic acid (4ACA), 2-(4-aminophenyl)aldehyde, 4-aminophenylacetic acid and 4-aminophenethylethanol (4APE), from carbon sources such as glucose by fermentation (see FIG. 1).

Thus, a method allowing industrial mass production of aniline derivatives including 4-aminophenylalanine (4APhe), 4-aminocinnamic acid (4ACA), 2-(4-aminophenyl)aldehyde, 4-aminophenylacetic acid and 4-aminophenethylethanol (4APE) from carbon sources such as glucose by fermentation has not yet been established, and there is strong demand to develop one.

CITATION LIST

Patent Literature

[PTL 1] International Patent Publication No. WO2013/073519
[PTL 2] CN103060352A Specification
[PTL 3] Japanese Patent Public Inspection No. 2008-501326

Non-Patent Literature

[NPL 1] He, et al., Microbiology (2001)
[NPL 2] Zhou, et al., Biotechnol Lett (2013) 35:751-756
[NPL 3] J. Am. Chem. Soc. 2003, 125, 935-939

DISCLOSURE OF THE INVENTION

Problems to be Solved by the Invention

As mentioned above, when the conventionally known pap genes, i.e. the 3 key enzymes known in pathways of antibiotic production (for example, PapA, PapB, PapC of *Streptomyces venezuelae*) are simply utilized directly, the productivity of 4-aminophenylalanine (4APhe) by fermentation is no more than about 0.2 g/L, and even attempting various combinations of conventionally known pap genes, it accumulates at no more than about 0.9 g/L. The present inventors have transferred enzyme genes associated with 4-aminocinnamic acid (4ACA) synthesis into transformants producing 0.2 to 0.9 g/L of 4APhe using conventional pap genes, but were not able to accomplish synthesis of 4ACA.

In light of the current situation of the prior art, it is an object of the invention to provide a method that allows industrial mass production of aniline derivatives including 4-aminophenylalanine (4APhe), 4-aminocinnamic acid (4ACA), 2-(4-aminophenyl)aldehyde, 4-aminophenylacetic acid and 4-aminophenethylethanol (4APE) by fermentation from a carbon source such as glucose.

Means for Solving the Problems

Upon searching for novel pap-like genes coding for proteins having homology with PapA, PapB, PapC of *Streptomyces venezuelae*, using genome databases, with the aim of increasing 4-aminophenylalanine (4APhe) productivity, and finding that *Pseudomonas fluorescence* SBW25 (De Leij F et al. (1995) Appl Environ Microbiol 61:3443-3453) strains PFLU1770, PFLU1771 and PFLU1772, which belong to the same phylum Proteobacteria as *Escherichia coli*, exhibit homology of 34% (PapC), 44% (PapA) and 28% (PapB), respectively, the present inventors succeeded in creating recombinant *Escherichia coli* producing the genes and in providing them for fermentation of 4-aminophenylalanine (4APhe), and were able to drastically increase productivity, with production of 4APhe at 1.8 g/L. It has not been possible in the prior art to achieve production of 4APhe on the order of grams.

Surprisingly, as mentioned above, it has not been possible to synthesize 4ACA even by transferring enzyme genes associated with synthesis of 4-aminocinnamic acid (4ACA) into transformants producing 4APhe at 0.2 to 0.9 g/L using conventional pap genes, but 4ACA were successfully synthesized for the first time when these enzyme genes were transferred into transformants producing 4APhe at 1.8 g/L. The present inventors conjecture that, while conversion from chorismic acid to 4-aminopyruvic acid in *Escherichia coli* has not proceeded efficiently by prior art methods, it can be efficiently promoted by gene modification, and as a result, 4APhe productivity is increased and the threshold for 4APhe production is exceeded, thereby allowing production of 4ACA which has not been achievable in the past. The present inventors conducted diligent research and repeated experimentation based on this finding, and thereupon completed this invention.

Specifically, the present invention is as follows.

[1] A method for producing an aniline derivative, comprising the following step:

transferring three or more exogenous genes into a microorganism having a function of biosynthesizing 4-aminophenylpyruvic acid from chorismic acid, to create a microorganism capable of producing 4-aminophenylalanine (4APhe) at 1.8 g/L or greater under prescribed culturing conditions; and contacting the microorganism with a carbon source under conditions suitable for growth and/or maintenance of the microorganism, to produce at least one aniline derivative selected from the group consisting of 4-aminophenylalanine (4APhe), 4-aminocinnamic acid (4ACA), 2-(4-aminophenyl)aldehyde, 4-aminophenylacetic acid and 4-aminophenethylethanol (4APE).

[2] The method according to [1] above, wherein the three or more exogenous genes are papA, papB and papC.

[3] The method according to [2] above, wherein the papA, papB and papC are each derived from *Pseudomonas fluorescence*.

[4] The method according to [3] above, wherein the papA, papB and papC comprise the sequences listed as SEQ ID NO: 7, 9 and 5, respectively.

[5] The method according to any one of [1] to [4] above, wherein in the step of creating the microorganism, at least one gene coding for phenylalanine synthase is further disrupted.

[6] The method according to [5] above, wherein the disrupted gene is pheA.

[7] The method according to any one of [1] to [6] above, wherein in the step of creating the microorganism, at least one exogenous gene selected from the group consisting of aroG, aro10 and pal is further transferred.

[8] The method according to any one of [1] to [7] above, wherein the microorganism is selected from the group consisting of *Escherichia coli, Bacillus, Corynebacterium, Pseudomonas* or *Zymomonas* bacteria and yeast belonging to *Saccharomyces* or *Schizosaccharomyces*.

[9] The method according to [8] above, wherein the microorganism is *Escherichia coli*.

[10] The method according to any one of [1] to [9] above, wherein the carbon source is selected from the group consisting of D-glucose, sucrose, oligosaccharides, polysaccharides, starch, cellulose, rice bran, molasses, corn decomposition solution and cellulose decomposition solution.

Effect of the Invention

By the method of the invention it is possible to accomplish industrial mass production of at least one aniline derivative selected from the group consisting of 4-aminophenylalanine (4APhe), 4-aminocinnamic acid (4ACA), 2-(4-aminophenyl)aldehyde, 4-aminophenylacetic acid and 4-aminophenethylethanol (4APE) by fermentation from a carbon source.

DESCRIPTION OF EMBODIMENTS

Figure 1:
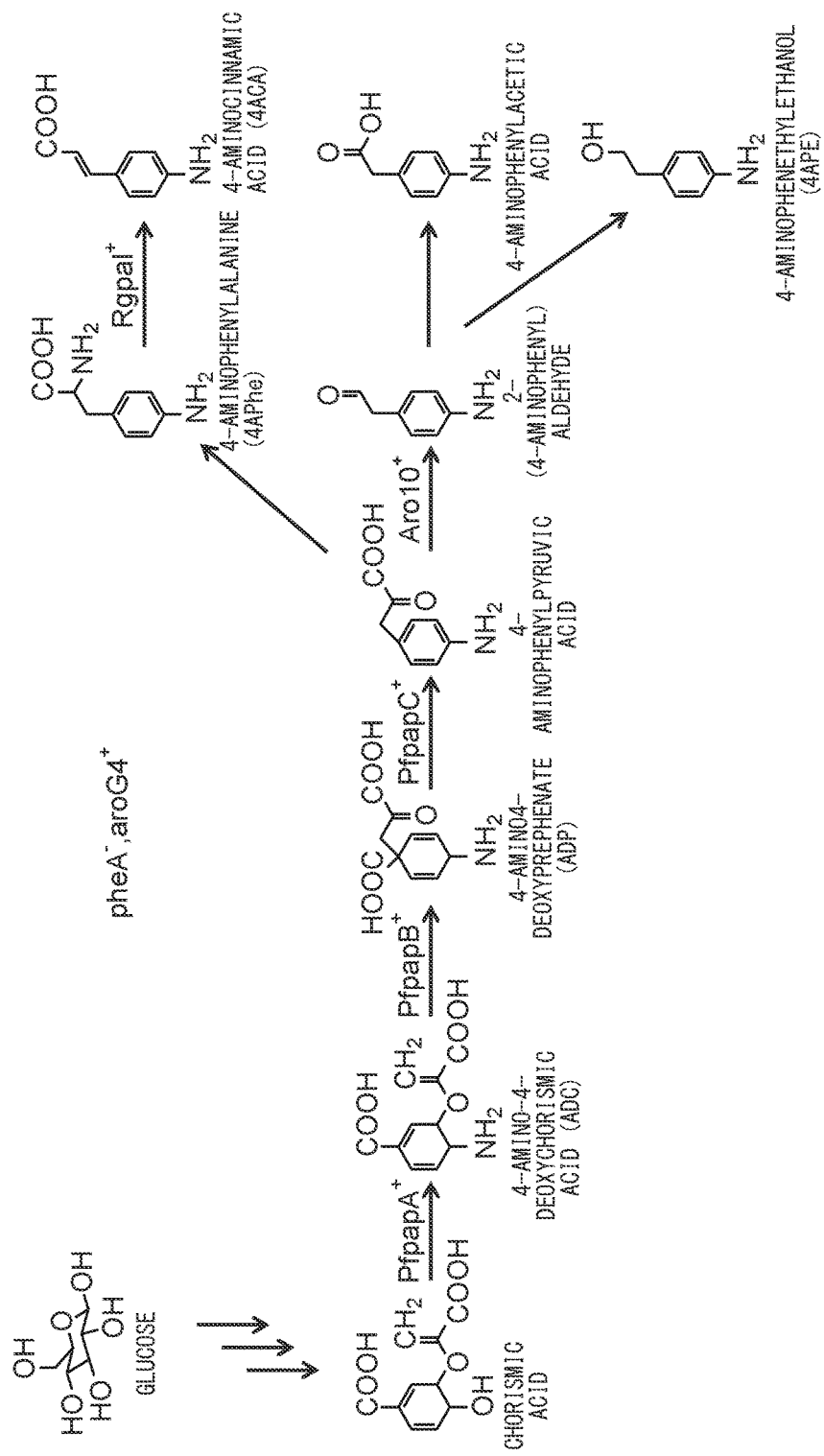
FIG. 1 is a schematic diagram showing the pathways leading from glucose to 4-aminophenylalanine (4APhe), 4-aminocinnamic acid (4ACA), 2-(4-aminophenyl)aldehyde, 4-aminophenylacetic acid and 4-aminophenethylethanol (4APE), via chorismic acid and 4-aminophenylpyruvic acid.

The invention will now be explained in detail by way of embodiments thereof.

Unless otherwise specified, all of the technical and scientific terms used throughout the present specification have the same meanings as generally understood by a person skilled in the technical field to which the present disclosure is related. Similar or equivalent methods or substances to those mentioned throughout the present specification may be used for carrying out the methods or compositions disclosed herein, the methods, apparatuses, substances, etc. mentioned in the present specification being examples.

The term "microorganism" includes prokaryotic microorganisms and eukaryotic microorganisms of the Archaea domain, Bacteria domain and Eukarya domain, the latter including yeast, filamentous fungi, protozoa, algae, and higher protists.

For this embodiment, the microorganism may be any one that has the function of biosynthesizing 4-aminophenylpyruvic acid from chorismic acid, but it is preferably one selected from the group consisting of *Escherichia coli, Bacillus, Corynebacterium, Pseudomonas* or *Zymomonas* bacteria and *Saccharomyces* or *Schizosaccharomyces* yeast, and from the viewpoint of rapid growth ability and ease of fermentation management, *Escherichia coli* is particularly preferred.

The terms "recombinant microorganism" and "recombinant host cells" are used interchangeably throughout the present specification, and they indicate a microorganism that has been genetically modified to produce or overproduce an endogenous polynucleotide, or to produce a foreign polynucleotide such as included in a vector, or having altered production of an endogenous gene. Here, "altered" means upregulation or downregulation of gene production, or the level of an RNA molecule coding for a polypeptide or polypeptide subunit or an equivalent RNA molecule, or the activity of one or several polypeptides or polypeptide subunits, resulting in increase or decrease of the production, level or activity compared to that observed in the unaltered state.

For a gene sequence, the term "production" refers to transcription of the gene and, where appropriate, translation of the obtained mRNA transcript into a protein. Thus, as is clear from context, protein production results from transcription and translation of an open reading frame sequence. The production level of a desired product in host cells can be determined based on the amount of corresponding mRNA in the cells, or the amount of desired product encoded by a selected sequence. For example, mRNA that has been transcribed from a selected sequence can be quantified by PCR or Northern hybridization (see Sambrook et al., Molecular Cloning: A Laboratory Manual, Cold Spring Harbor Laboratory Press (1989)). A protein encoded by a selected sequence can be quantified by various methods such as, for example, assay of the bioactivity of the protein by ELISA, using an antibody that reacts with the protein, recognizing and binding with it, or an assay that is independent of the activity, such as Western blotting or radioimmunoassay. See Sambrook et al. cited above. A polynucleotide generally codes for a target enzyme that participates in a metabolic pathway for production of a desired metabolite.

The terms "recombinant microorganism" and "recombinant host cells" are understood to indicate not only a specific recombinant microorganism but also any descendants or latent descendants of the microorganism. Because certain modifications may take place with subsequent generations due to mutations or environmental influences, such descendants are often not in fact identical to the parent cells, but as used herein, these are still included within the scope of the term.

The term "manipulation" refers to any treatment of a microorganism that produces a detectable change in the microorganism, the treatment including, but not being limited to, insertion of a foreign polynucleotide and/or polypeptide into the microorganism and mutation of a polynucleotide and/or polypeptide that is unique to the microorganism.

The terms "metabolically manipulated" or "metabolic manipulation" imply a rational pathway design or assembly of a biosynthesis gene, a gene associated with an operon, or a regulatory element for such a polynucleotide, for production of a desired metabolite. The term "metabolically manipulated" may further include optimization of metabolic flux, by reduction of competitive metabolic pathways that compete with intermediates through the desired pathway, or regulation or optimization of transcription, translation, protein stability and protein functionality using genetic engineering including disruption and knock-out, and appropriate culturing conditions.

The terms "metabolically manipulated microorganism" and "modified microorganism" are used interchangeably throughout the present specification, and refer not only to particular cells of interest but also to descendants or latent descendants of those cells. Because certain modifications may take place with subsequent generations due to mutations or environmental influences, such descendants are often not in fact identical to the parent cells, but as used herein, these are still included within the scope of the term.

The term "biosynthetic pathway", also known as "metabolic pathway", refers to a series of anabolic or catabolic biochemical reactions for conversion of one chemical species to another chemical species. When gene products act on the same substrate either in parallel or in series to produce the same product, or act on a metabolic intermediate (or "metabolite") between the same substrate and metabolic final product, or produce the metabolic intermediate, the gene products belong to the same "metabolic pathway".

The term "foreign (exogenous)", when used herein in reference to a molecule, and especially to an enzyme or polynucleotide, indicates a molecule being produced in an organism other than the organism from which the molecule is derived, or in an organism other than an organism found in nature, and it is unrelated to the production level, as the production level may be lower than, equal to or higher than the production level of the molecule in the naturally occurring microorganism.

The terms "natural" or "endogenous" when used herein in reference to a molecule, and especially to an enzyme or polynucleotide, indicates a molecule being produced in the organism from which the molecule is derived, or in an organism found in nature, and it is unrelated to the production level, as the production level may be lower than, equal to or higher than the production level of the molecule in the naturally occurring microorganism. It is understood that production of a natural enzyme or polynucleotide can be altered in a recombinant microorganism.

The term "feedstock" is defined as a starting material, or a mixture of starting materials, supplied to a microorganism or fermentation process, from which other products can be produced. For example, a carbon source such as a biomass or a carbon compound derived from a biomass is a feedstock for a microorganism that produces product fuel in a fermentation process. The feedstock may contain nutrients other than carbon sources.

The term "carbon source" generally refers to a substance suitable for use as a source of carbon, for prokaryotic organism growth or eukaryotic cell growth. Carbon sources include, but are not limited to, biomass hydrolysates, starch, sucrose, cellulose, hemicellulose, xylose, lignin and monomer components of these substrates. Without being limitative, carbon sources may include various organic compounds in various forms including polymers, carbohydrates, acids, alcohols, aldehydes, ketones, amino acids and peptides. Examples of these include various monosaccharides, for example, glucose, dextrose (D-glucose), maltose, oligosaccharides, polysaccharides, saturated or unsaturated fatty acids, succinic acid, lactic acid, acetic acid, ethanol, rice bran, molasses, corn decomposition solution, cellulose decomposition solution, and mixtures of the foregoing.

The term "substrate" or "appropriate substrate" refers to any substance or compound that is converted to another compound by the action of an enzyme, or that is intended for such conversion. The term includes not only a single type of compound but also any combination of compounds, such as a solution, mixture or other substance containing at least one substrate or its derivative. Furthermore, the term "substrate" includes not only compounds that provide a carbon source suitable for use as a starting material such as sugar, derived from a biomass, but also intermediate and final product metabolites used in pathways associated with the metabolically manipulated microorganisms described in the present specification.

The term "ferment" or "fermentation" is defined as a process in which a microorganism is cultured in a medium containing a starting material such as feedstock or nutrients, the microorganism converting the starting material such as feedstock to a product.

The term "prescribed culturing conditions" means the fermentation culturing conditions that are defined in the examples below.

The term "polynucleotide" is used interchangeably with the term "nucleic acid" throughout the present specification and refers to an organic polymer comprising two or more monomers including nucleotides, nucleosides or their analogs, and they include, but are not limited to, single-stranded or double-stranded sense or antisense deoxyribonucleic acid (DNA) of arbitrary length, and where appropriate, single-stranded or double-stranded sense or antisense ribonucleic acid (RNA) of arbitrary length, including siRNA. The term "nucleotide" refers to any of several compounds comprising a purine or pyrimidine base and a ribose or deoxyribose sugar bonded to a phosphate group, which are the structural units of nucleic acid bases. The term "nucleoside" refers to a compound comprising a purine or pyrimidine base bonded to deoxyribose or ribose, found in nucleic acids in particular (guanosine or adenosine). The term "nucleotide analog" or "nucleoside analog" means, respectively, a nucleotide or nucleoside in which one or more individual atoms are replaced by different atoms or different functional groups. Thus, the term "polynucleotide" includes nucleic acids, DNA or RNA of arbitrary length, as well as their analogs or fragments. A polynucleotide of three or more nucleotides is known as a nucleotide oligomer or oligonucleotide.

It is understood that the polynucleotides mentioned in the present specification include "genes", and the nucleic acid molecules in the present specification include "vectors" or "plasmids". Thus, the term "gene" refers to a polynucleotide coding for a specific sequence of amino acids constituting all or part of one or more proteins or enzymes, also known as a "structural gene", and may include a regulatory (non-transcribed) DNA sequence such as a promoter sequence, which sequence determines the conditions in which the gene is produced, for example. The transcribed region of a gene may include the untranslated region that includes the intron, 5'-untranslated region (UTR) and 3'-UTR, and the coding sequence.

The term "vector" is any means that allows propagation and/or migration of a nucleic acid between organisms, cells or cell components. A vector may be a virus, bacteriophage, provirus, plasmid, phagemid, transposon or an artificial chromosome, such as a YAC (yeast artificial chromosome) BAC (bacterial artificial chromosome) or PLAC (plant artificial chromosome), which is an "episome", i.e. a component that can spontaneously replicate and be incorporated into the chromosomes of host cells. The vector may be a naked RNA polynucleotide, a naked DNA polynucleotide, a polynucleotide comprising both DNA and RNA in the same chain, polylysine bonded DNA or RNA, peptide bonded DNA or RNA or liposome-bonded DNA, which are essentially not episomes, or the vector may be an organism including one or more of the aforementioned polynucleotide constructs, for example, an *Agrobacterium*, bacterium or the like.

The term "transformation" refers to the process in which a vector is transferred into host cells. The transformation (or transduction, or transfection) can be realized by any of several methods, including chemical substance transformation (for example, lithium acetate transformation), electroporation, microinjection, microprojectile bombardment (or particle bombardment-mediated delivery), and *Agrobacterium*-mediated transformation.

The term "enzyme", as used herein, refers to any substance that catalyzes or promotes one or more chemical or biochemical reactions, and usually includes enzymes that are completely or partially composed of polypeptides, although it may include enzymes composed of different molecules including polynucleotides.

The term "protein" or "polypeptide", as used herein, indicates an organic polymer composed of two or more amino acid monomers and/or its analog. When used throughout the present specification, the terms "amino acid" or "amino acid monomer" refer to any natural and/or synthetic amino acids including glycine and both D- or L-optical isomers. The term "amino acid analog" refers to an amino acid wherein one or more individual atoms has been replaced with different atoms or different functional groups. Thus, the term "polypeptide" includes any amino acid polymers of arbitrary length, including full length proteins and peptides, as well as their analogs and fragments. A polypeptide of three or more amino acids is referred to as a "protein oligomer" or "oligopeptide".

As mentioned above, the first mode of the invention is a method for producing an aniline derivative, comprising the following step:

transferring three or more exogenous genes into a microorganism having a function of biosynthesizing 4-aminophenylpyruvic acid from chorismic acid, to create a microorganism capable of producing 4-aminophenylalanine (4APhe) at 1.8 g/L or greater under prescribed culturing conditions; and contacting the microorganism with a carbon source under conditions suitable for growth and/or maintenance of the microorganism, to produce at least one aniline derivative selected from the group consisting of 4-aminophenylalanine (4APhe), 4-aminocinnamic acid (4ACA), 2-(4-aminophenyl)aldehyde, 4-aminophenylacetic acid and 4-aminophenethylethanol (4APE).

The three or more exogenous genes are preferably papA, papB and papC, and more preferably the papA, papB and papC are derived from *Pseudomonas fluorescence*, and more preferably the papA, papB and papC consist of the nucleotide sequences listed as SEQ ID NO: 7, 9 and 5, respectively.

According to the invention, however, the amino acid sequences encoded by the three or more exogenous genes include proteins that comprise amino acid sequences having at least 90% sequence identity with the amino acid sequences listed as SEQ ID NO: 8, 10 and 6, respectively, and having PapA, PapB and PapC enzyme activity, and the sequence identity may be at least 91%, 92%, 93%, 94%, 95%, 96%, 97%, 98% or 99%.

Here, the term "sequence identity" means, for two chains of polypeptide sequences (or amino acid sequences) or polynucleotide sequences (or nucleotide sequences), the quantity (number) of amino acid residues or nucleotides composing them that can be determined as identical between the two chains, in terms of the mutual agreement between them, meaning the degree of sequence correlation between two polypeptide sequences or two polynucleotide sequences. Identity can be easily calculated. Numerous methods are known for measuring identity between two polynucleotide sequences or polypeptide sequences, and the term "sequence identity" is well known to those skilled in the art.

Furthermore, according to the invention, the amino acid sequences encoded by the three or more exogenous genes include proteins that comprise the amino acid sequences listed as SEQ ID NO: 8, 10 and 6, respectively, with a deletion, substitution, insertion or addition of one or several amino acids, and having PapA, PapB and PapC enzyme activity. Here, "several" may be at most 10, 9, 8, 7, 6, 5, 4, 3 or 2.

Mutant DNA can be prepared by any method known to those skilled in the art such as, for example, chemical synthesis, genetic engineering or mutagenesis. Specifically, mutant DNA can be obtained by introducing mutations into DNA comprising the nucleotide sequences coding for the amino acid sequences listed as SEQ ID NO: 8, 10 and 6, using a method of contact with a chemical agent serving as a mutagen, a method of irradiation with ultraviolet rays or a genetic engineering method. Site-specific mutagenesis is a genetic engineering method that is useful as it allows introduction of specific mutations into specified sites, and it may be carried out by the method described in Sambrook, J. et al., Molecular Cloning: A Laboratory Manual, 2$^{nd}$ Ed., Cold Spring Harbor Laboratory Press, Cold Spring Harbor, N.Y., 1989. By producing the mutant DNA using a suitable production system, it is possible to obtain a protein comprising an amino acid sequence with a deletion, substitution, insertion or addition of one or several amino acids.

Furthermore, according to the invention, the three or more exogenous genes include nucleic acids comprising nucleotide sequences that hybridize with nucleic acid comprising nucleotide sequences complementary to the nucleotide sequences listed as SEQ ID NO: 7, 9 and 5 under high stringent conditions, and that code for proteins having PapA, PapB and PapC enzyme activity.

As used herein, "stringent conditions" are conditions that allow specific binding between a polynucleotide and genomic DNA in a selective and detectable manner. Stringent conditions are defined by an appropriate combination of salt concentration, organic solvent (for example, formamide), temperature and other known conditions. Specifically, stringency is increased by reducing the salt concentration, increasing the organic solvent concentration or raising the hybridization temperature. Stringency is also affected by the rinsing conditions after hybridization. The rinsing conditions are defined by the salt concentration and temperature, and stringency of rinsing is increased by reducing the salt concentration and raising the temperature. Thus, "stringent conditions" means conditions in which a specific hybrid is formed only between nucleotide sequences having high identity, namely a degree of identity between the nucleotide sequences of about 90% or greater as the overall average. Specifically, "stringent conditions" indicates hybridization with 6.0×SSC at about 45° C. followed by rinsing with 2.0×SSC at 50° C. For selection of stringency, the salt concentration in the rinsing step may be selected between, for example, about 2.0×SSC, 50° C. as low stringency to about 0.1×SSC, 50° C. as high stringency. Also, the temperature for the rinsing step may be raised from room temperature, or approximately 22° C., as low stringent conditions to about 65° C. as high stringent conditions. The hybridization can be carried out according to a method known to those skilled in the art or a similar method. When a commercially available library is to be used, it may be carried out according to the method described in the accompanying directions for use.

According to this embodiment, in the step of creating the microorganism, preferably at least one gene coding for phenylalanine synthase, such as pheA, is also disrupted. Also preferably, at least one exogenous gene selected from the group consisting of aroG, aro10 and pal is further introduced. Enzymes associated with the metabolic pathway of the invention will now be described.

Biosynthesis of 4-amino-4-deoxychorismic acid (ADC) from chorismic acid is publicly known from K. S. Anderson et al., JACS 113 (1991) 3198-3200. On p. 5690 of Parsons et al., Biochem 42(2003) 5684-5693, it is stated that ADC is only barely hydrolyzed under the influence of phenazine biosynthesis PhzD protein, for which ADC is clearly an unsatisfactory substrate. Moreover, since ADC synthesis is the first step in folate synthesis from chorismic acid in the natural world, aminodeoxychorismic acid synthase enzyme is abundantly available in the natural world. It has been speculated that these are to be found in all folate protrophic organisms, such as bacteria, yeast, plants and lower eukaryotes. The aminodeoxychorismic acid synthase enzyme is known to also participate in p-aminobenzoate synthesis.

According to the invention, a papA-like gene (PfpapA) was used, for which conversion activity from chorismic acid to 4-amino-4-deoxychorismic acid (ADC) had not been confirmed.

The biosynthetic pathway from 4-amino-4-deoxychorismic acid (ADC) to 4-amino-4-deoxyprephenate (ADP) is publicly known from Teng et al., J. Am. Chem. Soc. 107 (1985) 5008-5009, for example, but biosynthesis and collection of ADP was not described so as to be publicly known as for ADC, probably because the ADP product is unstable. This publication indicates possible biosynthetic pathways from 4-amino-4-deoxychorismic acid (ADC) and 4-amino-4-deoxyprephenate (ADP) to 4-aminophenylalanine (4APhe), similar to the disclosure of Blanc et al., Mol. Mic. 23(1997) 191-202, but the fermentation pathways of the ADC and ADP products to 4-aminophenylalanine (4APhe) and collection thereof, are in no way suggested. As mentioned above, PTL 3 discloses that biosynthesis of 4-amino-4-deoxychorismic acid (ADC), at least catalyzed by an enzyme belonging to the class of aminodeoxychorismic acid synthases, is carried out by in vivo fermentation in a host microorganism having 4-amino-4-deoxychorismic acid synthase at an increased level of activity, while obtaining a fermentation culture broth including 4-amino-4-deoxychorismic acid (ADC) and 4-amino-4-deoxyprephenate (ADP), and that the compounds are recovered from the fermentation culture broth, either together or each one separately.

According to the invention, a papB-like gene (PfpapB) was used, for which conversion activity from 4-amino-4- deoxychorismic acid (ADC) to 4-amino-4-deoxyprephenate (ADP) had not been confirmed.

The enzyme 4-amino-4-deoxyprephenate dehydrogenase participates in the biosynthetic pathway from 4-amino-4-deoxyprephenate (ADP) to 4-aminophenylpyruvic acid. The enzyme 4-amino-4-deoxyprephenate dehydrogenase carries out oxidative decarboxylation of ADP, causing dissociation of the carboxy group at position 1 of ADP and producing 4-aminophenylpyruvic acid which has an aromatic ring. According to the invention, a papC-like gene (PfpapC) was used, for which conversion activity from 4-amino-4-deoxyprephenate (ADP) to 4-aminophenylpyruvic acid had not been confirmed.

An aminotransferase participates in the biosynthetic pathway from 4-aminophenylpyruvic acid to 4-aminophenylalanine (4APhe). Aminotransferases transfer amino groups of amino acids to $\alpha$-keto acid, and tyrosine aminotransferase, aspartic acid aminotransferase and the like have been shown to participate in the biosynthesis of aromatic amino acids. In this case, glutamic acid is utilized as an amino group donor. According to the invention, an endogenous enzyme of the host microorganism was used for conversion from 4-aminophenylpyruvic acid to 4-aminophenylalanine (4APhe).

Ammonia-lyases participate in the biosynthetic pathway from 4-aminophenylalanine (4APhe) to 4-aminocinnamic acid (4ACA). Ammonia-lyases are enzymes such as phenylalanine ammonia-lyase, tyrosine ammonia-lyase and histidine ammonia-lyase that cause dissociation of $\alpha$-amino groups of aromatic amino acids to produce $\alpha$-$\beta$-unsaturated carboxylic acids and ammonia, and those derived from plants and microorganisms such as NCBI (www.ncbi.nlm.nih.gov/gene/) deposit number NP 187645.1, NCBI deposit number DQ013364.1, NCBI deposit number EGU13302.1 and NCBI deposit number KF770992.1, are preferred.

Phenylalanine ammonia-lyase (Pal) is an enzyme having activity of converting phenylalanine to cinnamic acid, and resting cells reaction using *Escherichia coli* producing Pal4 genes of Arabidopsis thaliana (the wild type and mutants F126E and F126D), or the PAL gene (RgPal) of *Rhodotorula glutinis*, and conversion of 4APhe to 4ACA, has already been successfully achieved.

According to the invention, RgPal was used for conversion from 4-aminophenylalanine (4APhe) to 4-aminocinnamic acid (4ACA).

A decarboxylase participates in the biosynthetic pathway from 4-aminophenylpyruvic acid to 2-(4-aminophenyl)aldehyde. A decarboxylase is an enzyme that causes dissociation of a carboxyl group from a pyruvic acid derivative to produce an aldehyde derivative and carbon dioxide, there being especially used ones that can utilize aromatic pyruvic acid derivatives such as phenylpyruvic acid as substrates. The yeast-derived phenylpyruvate decarboxylase (NCBI deposit number NM_001180688.3) is used for this purpose, and analogous enzymes such as NCBI deposit number XP_002498188 and NCBI deposit number XP_444902.1 can also be used.

For conversion from 4-aminophenylpyruvic acid to 2-(4-aminophenyl)aldehyde according to the invention there was used the yeast Aro10, which has been demonstrated to be a phenylpyruvate decarboxylase that converts phenylpyruvic acid to phenylacetaldehyde.

Aldehyde dehydrogenases participate in the biosynthetic pathway from 2-(4-aminophenyl)aldehyde to 4-aminophenylacetic acid. An aldehyde dehydrogenase oxidizes an aldehyde to yield carboxylic acid, with $NAD^+$ or $NADP^+$ as a coenzyme, and any of those derived from prokaryotic or eukaryotic organisms may be used. In particular, those utilizing aromatic aldehydes such as phenylacetaldehyde as substrates may be used. More particularly, NCBI deposit number NP_013893.1 and NCBI deposit number NP_013892.1, which are yeast-derived phenylacetaldehyde dehydrogenases, as well as their analogous enzymes, may be used for this purpose.

Alcohol dehydrogenases participate in the biosynthetic pathway from 2-(4-aminophenyl)aldehyde to 4-aminophenethylethanol (4APE). An alcohol dehydrogenase reduces an aldehyde to an alcohol with NADH or NADPH as a coenzyme, and any of those derived from prokaryotic or eukaryotic organisms may be used. In particular, those utilizing aromatic aldehydes such as phenylacetaldehyde as substrates may be used. More particularly, NCBI deposit number NP_014555.1, NCBI deposit number NP_014032.1, NCBI deposit number NP_013800.1, NCBI deposit number NP_011258.1 and NCBI deposit number NP_009703.1, which are yeast-derived alcohol dehydrogenases, as well as their analogous enzymes, may be used for this purpose. Those derived from aniline derivative-producing hosts, produced by the producing hosts, may also be used.

According to the invention, an endogenous enzyme of a host microorganism was used for conversion from 2-(4-aminophenyl)aldehyde to 4-aminophenethylethanol (4APE).

Also, *Escherichia coli* AroG and AroF are enzymes that catalyze the initial reaction in the biosynthetic pathway for aromatic amino acids, and they are used for synthesis of 3-deoxy-D-arabino-heptulosonic acid 7-phosphate. The enzyme activity of AroG is known to be inhibited by phenylalanine. Mutant AroG, which is resistant to feedback inhibition, is utilized for high production of aromatic amino acids and their analogs using *Escherichia coli*, and AroG4 is a mutant form of AroG. Therefore, transfer of AroG4 was carried out in the examples that follow.

In addition, *Escherichia coli* PheA is an enzyme involved in phenylalanine synthesis, having activity of converting chorismic acid (chorismate) to phenylpyruvic acid (phenylpyruvate). Since chorismic acid is also a substrate of PapA, disruption of the pheA gene would be expected to result in increased host cell concentration of chorismic acid which is the substrate of PapA. Therefore, the pheA gene was disrupted in the examples which follow.

EXAMPLES

The present invention will now be explained in greater detail by the following examples.

[Fermentation Medium Composition]

Figures 2, 3:
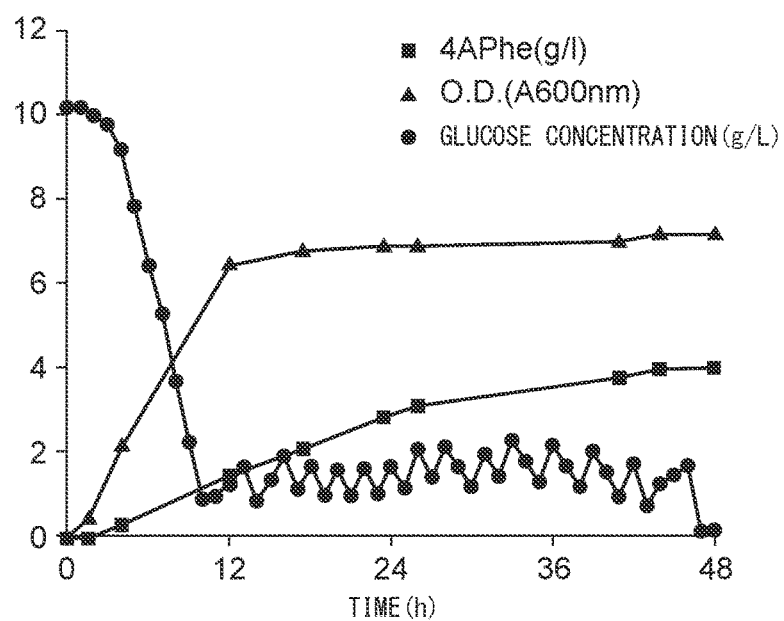
FIG. 2 is a table showing the fermentation medium composition.
FIG. 3 is a graph showing 4APhe production by PFAB-CAAro.

The fermentation medium composition is shown in FIG. 2. The following culturing conditions were used for the fermentation, and are referred to as "prescribed culturing conditions" throughout the present specification.

[Prescribed Culturing Conditions]

(Preculturing)

LB medium was added to a test tube at up to 4 ml of liquid volume, and then 100 µl of *Escherichia coli* glycerol stock was added thereto and culturing was conducted at 37° C., 120 rpm for 6 hours.

(Medium Composition (/L))

The LB medium composition was as shown in Table 1. The culture media used were sterilized at 121° C., 15 minutes using an autoclave.

TABLE 1

| LB medium pH 7.0 | |
|---|---|
| Tryptone | 10 g/L |
| Yeast extract | 5 g/L |
| NaCl | 10 g/L |

(Main Culturing)

A 5 ml portion of the fermentation medium was added to a 50 ml test tube, and then 500 µl of preculturing broth was added thereto and culturing was conducted at 37° C., 120 rpm for 12 hours. Next, IPTG was added to a final concentration of 0.1 mM, and culturing was continued for 12 hours. For culturing using a flask, 100 ml of the aforementioned fermentation medium with glucose added to a final concentration of 10 g/l was added to a 500 ml blade-equipped flask, 500 µl of preculturing broth was added thereto, and culturing was continued at 30° C. As the producing host there was used Escherichia coli NST37(DE3) [ATCC 31882, U.S. Pat. No. 4,681,852, genotypes: aroG, aroF, pheA, tyrR, tyrA and trpE] or a derivative thereof, and tyrosine and tryptophan were added to the medium at 0.05 g/l. After inducing production with IPTG, glucose was added every 12 hours of culturing to 5 g/l. After 36 hours of culturing, the amount of production of 4APhe as the compound to be evaluated was examined.

[Preparation of Bacterial Strains]
(Preparation of pheA Gene-Disrupted Strain)

Following the procedure reported in Baba, T. et al. Mol. Syst. Biol. 2, 2006.0008 (2006), the kanamycin resistance gene was amplified using a primer set comprising a sequence homologous with 50 bp outside of the ORF of the pheA gene, and the FRT sequence (SEQ ID NO: 4: 5'-gt-gaaaacagtacgggtactgtactaaagtcacttaaggaaacaaacatggaagttc-ctattct ctagaaagtataggaacttctggacagcaagcgaaccggaattgc-3'; and SEQ ID NO: 3: 5'-gatgattcacatcatccggcaccttttcatcaggt-tggatcaacaggcacgaagttcctatact ttctagagagaataggaacttctca-gaagaactcgtcaagaaggcg-3'), with pZE21 MCS (Lutz and Bujard, Nucl. Acids Res. (1997) 25(6): 1203-1210) as template. The obtained gene fragment was used as a disruption cassette. The region comprising the pheA gene in the genome of strain NST37 [ATCC 31882, U.S. Pat. No. 4,681,852, genotypes: aroG, aroF, pheA, tyrR, tyrA, trpE] was replaced with a disruption cassette by $Red^R/ET^R$ Recombination, to obtain a pheA gene-disrupted strain. The kanamycin resistance gene in the genome of the gene-disrupted strain was removed with an FLP-FRT recombination system. The obtained pheA gene-disrupted strain was designated as NST37(DE3)/ΔpheA. This strain could not grow in phenylalanine-free M9 medium.

(Construction of Plasmids for aroG4 and aroF Production)

The artificial gene synthesis service of GeneScript was used to synthesize a DNA fragment comprising the aroG4 gene with EcoRI and HindIII cleavage sites at the ends (SEQ ID NO: 1, Appl. Environ. Microbiol., 63, 761-762(1997)). After smoothing with T4 DNA Polymerase, it was linked to pACYC184 (Nippon Gene) having the chloramphenicol resistance gene previously cut with EcoRV. The obtained plasmid was designated as pACYC-aroG4. This was transferred into NST37(DE3)/ΔpheA to create strain NST37 (DE3)/ΔpheA/pACYC-aroG4.

(Construction of Plasmids for PFLU1770, PFLU1771 and PFLU1772 Production)

Upon searching for genes coding for proteins exhibiting homology with PapABC of Streptomyces venezuelae, using genome databases, it was found that Pseudomonas fluorescence SBW25 (De Leij F et al. (1995) Appl Environ Microbiol 61:3443-3453) strains PFLU1770, PFLU1771 and PFLU1772, which belong to the same phylum Proteobacteria as Escherichia coli, exhibited homology of 34% (PapC), 44% (PapA) and 28% (PapB), respectively. Recombinant Escherichia coli producing these genes were prepared, and the production of 4APhe was examined.

The artificial gene synthesis service of GeneScript was used to synthesize the PFLU1770 gene (SEQ ID NO: 5, PfPapC gene), PFLU1771 gene (SEQ ID NO: 7, PfPapA gene) and PFLU1772 gene (SEQ ID NO: 9, PfPapB gene) of Pseudomonas fluorescence SBW25, which belong to the same phylum Proteobacteria as Escherichia coli. The codons of the nucleotide sequence of each gene were optimized for production in Escherichia coli. Each gene linked to pUC57 (Genescript) was cut using different restriction enzymes and linked with pETduet-1 (Novagen), pRSF-duet-1 (Novagen) or pCDFduet-1 (Novagen) to construct pET-PFLU1771, pRSF-PFLU1771, pCDF-PFLU1771, pET-PFLU1770_1772, pRSF-PFLU1770_1772 and pCDF-PFLU1770_1772. That is, PFLU1771 (PfpapA) was synthesized artificially and introduced into pETduet-1 to prepare pET-PFLU1771. Also, PFLU1770 (PfpapC) and PFLU1772 (PfpapB) were synthesized artificially and inserted into pCDFduet-1 to prepare pCDF-PFLU_1770_1772.

(Construction of SvpapABC and SppapBC Production Plasmids)

The following three plasmids were prepared. The PCR template used was total DNA of Streptomyces venezuelae (ATCC deposit number 10712) and Streptomyces pristinaespiralis (ATCC deposit number 25486).

pET-svpapA: A DNA fragment comprising the svPapA gene (He et al., Microbiol, 147: 2817-2829 (2001)) was amplified by PCR using the following primer pair (SEQ ID NO: 11:5'-gacacatatgcgcacgcttctgatcgac-3' and SEQ ID NO: 12:5'-gacgatatcatcgggcgcccgccacggc-3'). It was digested using restriction enzymes NdeI and EcoRV, and linked with pETduet-1 that had been treated with the same enzymes, to obtain pET-svpapA.

pRSF-svpapBC: A DNA fragment comprising the svPapB gene (He et al., Microbiol, 147: 2817-2829 (2001)) was amplified by PCR using the following primer pair (SEQ ID NO: 13:5'-gagccatgggcaccgagcagaacgagctg-3' and SEQ ID NO: 14:5'-cagaagcttcaccgccggtcctcggccgtc-3'). It was digested using restriction enzymes NcoI and HindIII, and linked with pRSFduet-1 that had been treated with the same enzymes, to obtain a plasmid. At the NdeI-XhoI site of the obtained plasmid, there was linked a DNA fragment comprising the svPapC gene (He et al., Microbiol, 147: 2817-2829 (2001)) obtained by amplification by PCR using the following primer pair (SEQ ID NO: 15:5'-cagagacatatgagcg-gcttccccgcag-3' and SEQ ID NO: 16:5'-gactcgagtcatcggtc-cttctcgccttcg-3'), to obtain pRSF-svpapBC.

pRSF-sppapBC: A DNA fragment comprising the spPapB gene (Blanc et al., Mol. Microbiol. 23: 191-202 (1997)) was amplified by PCR using the following primer pair (SEQ ID NO: 17:5'-cagccatgggcaccccgcccgccatcccc-3' and SEQ ID NO: 18:5'-cagaagcttcacgacacggccccccgcg-3'). It was digested using restriction enzymes NcoI and HindIII, and linked with pRSFduet-1 that had been treated with the same enzymes, to obtain a plasmid. At the NdeI-EcoRV site of the obtained plasmid there was linked a DNA fragment comprising the spPapC gene (Blanc et al., Mol. Microbiol. 23: 191-202 (1997)) obtained by amplification by PCR using the following primer pair (SEQ ID NO: 19:5'-cagagacatat-gaggggtggttcggtgttcg-3' and SEQ ID NO: 20:5'-cagatatca-gtgcagggcggtgaacatc-3'), to obtain pRSF-sppapBC.

(Construction of Plasmid for Aro10 Production)

The Aro10 gene (SEQ ID NO: 23) was amplified by PCR, with the genome of *Saccharomyces cerevisiae* S288C (ATCC 204508) as template, using the following primer pair (SEQ ID NO: 21:5'-gagccatggcacctgttacaattga-3' and SEQ ID NO: 22:5'-gacggatcctatttttatttcttttaaagtgc-3'). It was digested using restriction enzymes NcoI and BamHI, and linked with pRSF-duet1 that had been treated with the same enzymes, to obtain pRSF-aro10.

(Preparation of pET-PFLU1771 Rgpal)

A DNA fragment comprising the PAL gene derived from yeast *Rhodotorula glutinis* (SEQ ID NO: 27) (RgPAL gene) was amplified by PCR using the following primer pair (SEQ ID NO: 25:5'-gacggatccgatggcccctccgtcgactc-3' and SEQ ID NO: 26:5'-gctgaattcttatgccatcatcttgacgag-3'). It was digested using restriction enzymes BamHI and EcoRI and linked to pET-PFLU1771 that had been treated with the same enzymes, to obtain pET-PFLU_1771 Rgpal.

(Preparation of pRSF-Rgpal)

A DNA fragment comprising the RgPAL gene was amplified by PCR using the following primer pair (SEQ ID NO: 25 and SEQ ID NO: 26). It was digested using restriction enzymes BamHI and EcoRI, and linked with pRSFduet-1 that had been treated with the same enzymes, to obtain pRSF-Rgpal.

[Culturing Using Jar Fermenter]

A preculturing broth cultured in LB medium was seeded at a 1/10 volume in a 1.0 L-volume jar fermenter (BMJ-1: Biotto) containing 500 ml of medium for 4APhe production. Aeration was with air at 0.6 L/min, and the stirring speed was set to 500 r.p.m. When the O.D. reached 0.4 to 0.5, IPTG was added to a final concentration of 0.1 mM. A BF510 feed control system (Able-Biott) was used for culturing with glucose-stat. The BF510 was set so that the glucose concentration was measured each hour during this time, and when the measured value fell below 1.5 g/l, 1 g of glucose and 0.2 g of ammonium chloride were added to the culturing vat.

[Analysis of Samples]

The cell concentration was measured at 600 nm using a spectrophotometer (UVmini-1240). Measurement of the glucose concentration was accomplished by colorimetry, using a glucose test kit (Wako). For measurement of the 4APhe concentration in the medium, an HPLC (1200 infinity series: Hewlett Packard) was used and the absorbances at wavelengths of 210, 254 and 280 nm were measured as indices.

Example 1

The plasmids pET-PFLU1771 and pCDF-PFLU1770_1772 were transferred into *Escherichia coli* NST37(DE3)/ΔpheA/pACYC-aroG4 to obtain strain PFABCΔAro. Each strain was cultured under the aforementioned "prescribed culturing conditions" with an IPTG concentration of 0.1 mM, and after 36 hours of culturing, the amount of 4APhe production was examined. As a result, strain PFABCΔAro produced 1.8 g/L of 4APhe.

Comparative Example 1

When *Streptomyces pristinaespiralis* papABC (pET-sp-PapA and pRSF-spPapBC) was used by the same method as Example 1, 0.2 g/L of 4APhe was obtained. Also, when *Streptomyces venezuelae* papA (pET-svpapA) and *Streptomyces pristinaespiralis* papBC (pRSF-sppapBC) were used, 0.9 g/L of 4APhe was obtained, but the results of Example 1 were not reached.

Example 2: Culturing of Strain PFABCΔAro with Jar Fermenter

Upon culturing using strain PFABCΔAro, by the method described above in [Culturing using jar fermenter], 4APhe was successfully produced at a maximum of 4.0 g/L (sugar-based yield: 15%), as shown in FIG. 3. The sugar-based yield was 13% at 44 hours of culturing when the production volume no longer varied.

Example 3: Production of 4-Aminocinnamic Acid (4ACA)

The three plasmids pET-PFLU1771_Rgpal, pCDF-PFLU1770_1772 and pRSF-Rgpal were transferred into *Escherichia coli* NST37(DE3)/ΔpheA/pACYC-aroG4. The obtained strains were cultured using a jar fermenter, and 3 mg/L of 4ACA was produced.

Comparative Example 2

Contrasting with the above results, when a conventional pap gene was used under the same culturing conditions as Example 3, it was not possible to produce 4ACA.

Example 4: Production of 4-Aminophenethylethanol (4APE)

It was attempted to accomplish fermentative production of 4APE using yeast Aro10. A strain obtained by transferring pRSF-aro10 into PFABCΔAro was cultured. During this time, accumulation of 4APE was confirmed after 24 hours of culturing at both IPTG concentrations of 0.1 mM and 0.3 mM.

INDUSTRIAL APPLICABILITY

By the method of the invention it is possible to accomplish industrial mass production of at least one aniline derivative selected from the group consisting of 4-aminophenylalanine (4APhe), 4-aminocinnamic acid (4ACA), 2-(4-aminophenyl)aldehyde, 4-aminophenylacetic acid and 4-aminophenethylethanol (4APE) by fermentation from a carbon source.

SEQUENCE LISTING

What is claimed is:

1. A method for producing an aniline derivative, comprising the following steps:
transferring three or more exogenous genes into a microorganism having a function of biosynthesizing 4-aminophenylpyruvic acid from chorismic acid, to create a microorganism capable of producing 4-aminophenylalanine (4APhe) at 1.8 g/L or greater under prescribed culturing conditions; and
contacting the microorganism with a carbon source under conditions suitable for growth and/or maintenance of the microorganism, to produce at least one aniline derivative selected from the group consisting of 4-aminophenylalanine (4APhe), 4-aminocinnamic acid (4ACA), 2-(4-aminophenyl)aldehyde, 4-aminophenylacetic acid and 4-aminophenethylethanol (4APE), wherein the three or more exogenous genes are papA, papB and papC each derived from *Pseudomonas fluorescence*.

2. The method according to claim 1, wherein the papA, papB and papC consist of the nucleotide sequences listed as SEQ ID NO: 7, 9 and 5, respectively.

3. The method according to claim 1, where in the step of creating the microorganism, at least one gene coding for phenylalanine synthase is further disrupted.

4. The method according to claim 3, wherein the disrupted gene is pheA.

5. The method according to claim 1, where in the step of creating the microorganism, at least one exogenous gene selected from the group consisting of aroG, aro10 and pal is further transferred.

6. The method according to claim 1, wherein the microorganism is selected from the group consisting of *Escherichia coli*, *Bacillus*, *Corynebacterium*, *Pseudomonas* or *Zymomonas* bacteria, and yeast belonging to *Saccharomyces* or *Schizosaccharomyces*.

7. The method according to claim 6, wherein the microorganism is *Escherichia coli*.

8. The method according to claim 1, wherein the carbon source is selected from the group consisting of D-glucose, sucrose, oligosaccharides, polysaccharides, starch, cellulose, rice bran, molasses, corn decomposition solution, and cellulose decomposition solution.

* * * * *